US006998251B2

(12) United States Patent
Guttman et al.

(10) Patent No.: US 6,998,251 B2
(45) Date of Patent: Feb. 14, 2006

(54) NANOPOROUS MEMBRANE REACTOR FOR MINIATURIZED REACTIONS AND ENHANCED REACTION KINETICS

(75) Inventors: Andras Guttman, San Diego, CA (US); Zsolt Ronai, Szekesfehervar (HU); Csaba Barta, Budapest (HU)

(73) Assignee: Syngenta Participations AG, Basel (CH)

( * ) Notice: Subject to any disclaimer, the term of this patent is extended or adjusted under 35 U.S.C. 154(b) by 385 days.

(21) Appl. No.: 10/047,438

(22) Filed: Jan. 14, 2002

(65) Prior Publication Data

US 2003/0135030 A1 Jul. 17, 2003

Related U.S. Application Data

(60) Provisional application No. 60/367,378, filed on Jan. 12, 2001, now abandoned.

(51) Int. Cl.
| | |
|---|---|
| C12P 1/00 | (2006.01) |
| C12N 11/00 | (2006.01) |
| G01N 1/00 | (2006.01) |
| B01D 61/14 | (2006.01) |

(52) U.S. Cl. .................. 435/41; 204/452; 204/455; 204/605; 436/174; 530/420; 977/DIG. 1

(58) Field of Classification Search .............. 204/452, 204/455, 605; 435/41; 436/174; 977/DIG. 1; 530/420

See application file for complete search history.

(56) References Cited

U.S. PATENT DOCUMENTS

| 3,791,933 A | 2/1974 | Moyer et al. |
| 4,200,690 A | 4/1980 | Root et al. |
| 5,032,504 A | 7/1991 | Mauck |
| 5,064,764 A | 11/1991 | Besnainon et al. |
| 5,071,909 A | 12/1991 | Pappin et al. |
| 5,085,986 A | 2/1992 | Mauck et al. |
| 5,242,804 A | 9/1993 | Bahar et al. |
| 5,370,777 A * | 12/1994 | Guttman et al. ............ 204/452 |
| 5,830,680 A | 11/1998 | Meyerhoff et al. |
| 5,990,373 A | 11/1999 | Klabunde |
| 6,015,714 A | 1/2000 | Baldarelli et al. |
| 6,057,488 A | 5/2000 | Koper et al. |

OTHER PUBLICATIONS

Cassel, et al., *Electrophoresis*, 19:1341-1346, 1998, "Membrane-Mediated Sample Loading for Automated DNA Sequencing."

Dolnik, et al., *Electrophoresis*, 21:41-54, 2000, "Capillary Electrophoresis on Microchip."

Gerstner, et al., *Bio Techniques*, 28(4):628, 630, 2000, "Sequencing Difficult DNA Templates Using Membrane-Mediated Loading with Hot Sample Application." (One full page of advertisements not included.).

Guttman, *Analytical Chemistry*, 71(16):3598-3602, 1999, "Sample Stacking during Membrane-Mediated Loading in Automated DNA Sequencing."

Guttman, *LC/GC Magazine*, 17:1020-1026, 1999, "Automated DNA Fragment Analysis by High Performance Ultra-Thin-Layer Agarose Gel Electrophoresis." (Two full pages of advertisements not included.).

Guttman, et al., *Electrophoresis*, 21:3952-3964, 2000, "Ultrathin-Layer Gel Electrophoresis of Biopolymers."

Jacobson, et al., *Anal. Chem.*, 68:720-723, 1996, "Integrated Microdevice for DNA Restriction Fragment Analysis."

Sigma, Promotion Code SI-400, 2000, "Repetitive Gel Loading Slowing You Down? QuickComb™-96 The Speedy Solution."

International Search Report (ISR) for corresponding PCT Appl. No. PCT/US02/00993 dated Sep. 20, 2004.

Deamer et al., "Nanopores and Nucleic Acids: Propects for Ultrarapid Sequencing", *Elsevier Science Ltd.*, vol. 18, pp. 147-151, Apr. 2000.

Kasianowicz et al., "Characterization of Individual Polynucleotide Molecules Using a Membrane Channel", *Proc. Natl. Acad. Sci.*, pp. vol. 93, pp. 13770-13773, Nov. 1996.

Memo Concerning the Official Action Reported in the Covering Letter for Australian Patent Application No. 2002239906 dated May 12, 2005.

* cited by examiner

*Primary Examiner*—Ralph Gitomer
*Assistant Examiner*—Kailash C. Srivastava
(74) *Attorney, Agent, or Firm*—Jenkins, Wilson & Taylor, P.A.

(57) ABSTRACT

Reactors and methods for miniaturized reactions having enhanced reaction kinetics. In particular the subject matter is directed to chemical and biological reactions conducted in a nanoporous membrane environment. The subject matter contemplates methods for modifying the kinetics of reactions and devices for conducting reactions having modified kinetics. The subject matter also provides systems for rapid miniaturized reactions. Further the subject matter includes methods and kits for conducting a reaction with enhanced throughput and methods of conducting miniaturized, high throughput analyses of reaction products, and the like. Reactions performed on or within a nanoporous membrane exhibits improved kinetic characteristics.

18 Claims, 15 Drawing Sheets

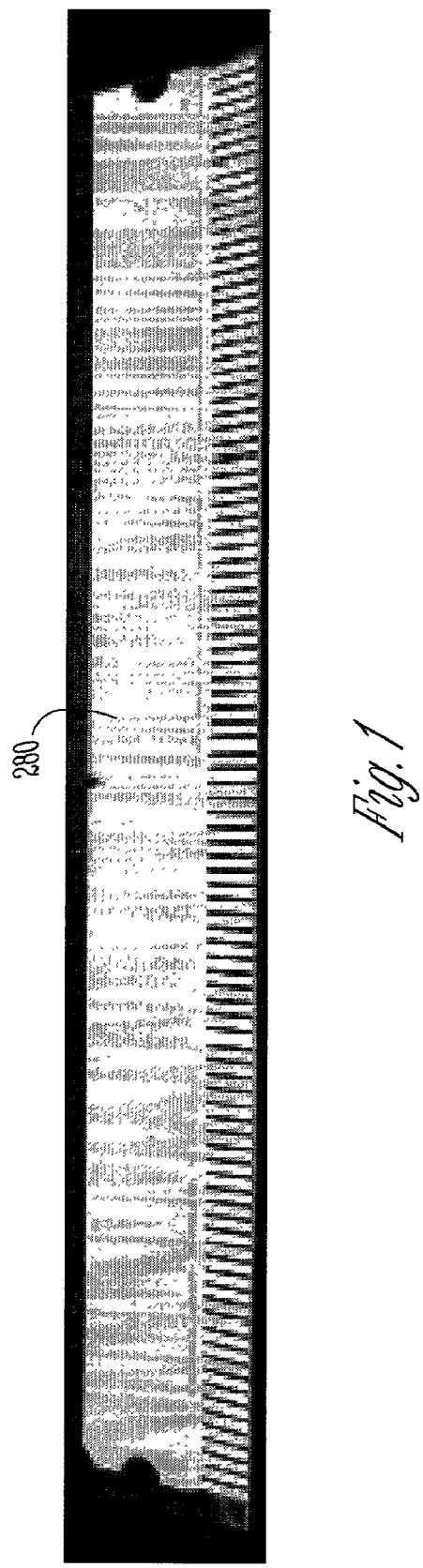

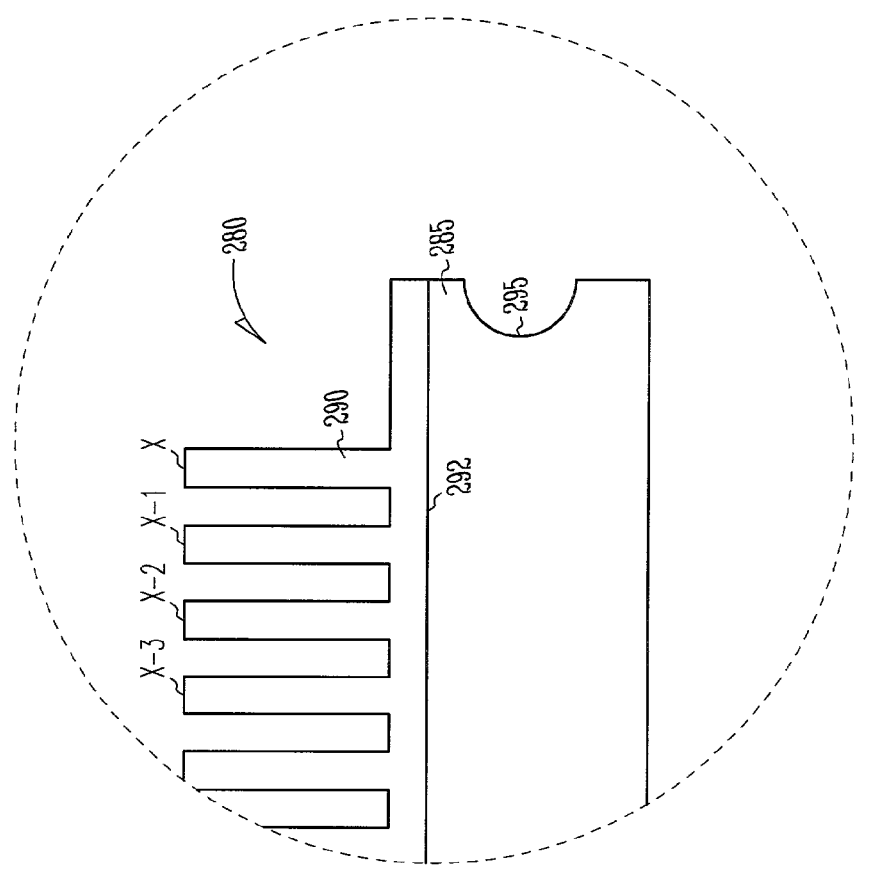
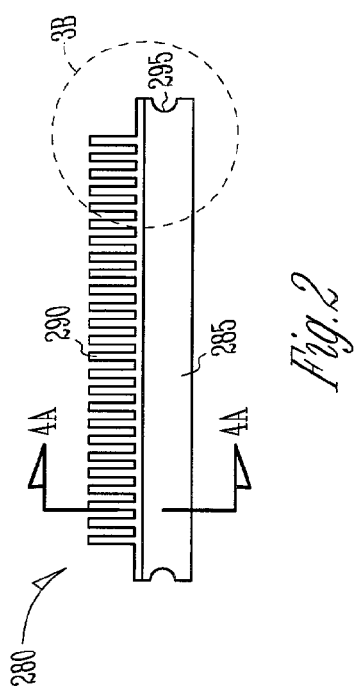

SEQUENCE LISTING

```
<160> NUMBER OF SEQ ID NOS: 2

<210> SEQ ID NO 1
<211> LENGTH: 18
<212> TYPE: DNA
```

-continued

```
<213> ORGANISM: Artificial
<220> FEATURE:
<223> OTHER INFORMATION: Forward PCR primer for amplification of a 101
      bp fragment of the pUC 19 cloning vector.

<400> SEQUENCE: 1
gtaaaacgac ggccagtg                                                      18

<210> SEQ ID NO 2
<211> LENGTH: 19
<212> TYPE: DNA
<213> ORGANISM: Artificial
<220> FEATURE:
<223> OTHER INFORMATION: Reverse PCR primer for amplification of a 101
      bp fragment of the pUC 19 cloning vector.

<400> SEQUENCE: 2
ggaaacagct atgaccatg                                                     19
```

NANOPOROUS MEMBRANE REACTOR FOR MINIATURIZED REACTIONS AND ENHANCED REACTION KINETICS

RELATED APPLICATIONS

This application claims priority to U.S. Provisional Application Ser. No. 60/367,378 now abandoned, arising from non-provisional U.S. patent application Ser. No. 09/759,989, (entitled NANOPOROUS MEMBRANE REACTOR FOR MINIATURIZED REACTIONS AND ENHANCED REACTION KINETICS, and filed on Jan. 12, 2001), the specification of which is herein incorporated by reference.

TECHNICAL FIELD

The present subject matter relates generally to reactors and methods involving miniaturized reactions having enhanced reaction kinetics and particularly, but not by way of limitation, to chemical and biological reactions conducted using a nanoporous membrane.

BACKGROUND

Many academic and industrial pursuits involve chemical and biological reactions. For example, genome sequencing, genetic engineering and genetic marker detection are important to those engaged in biotechnology research and development. In addition, organic synthesis, combinatorial chemistry, and high throughput screening reactions, and other kinds of chemical reactions used to identify new medicines are important to pharmaceutical research and development efforts.

Among the cost of the research and development is the time required for the chemical reaction and the cost of the reagents. Since ambiguous results or incomplete reactions are highly undesirable, arbitrarily shortening reaction times to save costs and accelerate the pace of research is not a viable option.

What is needed is a system and method for reducing the cost of conducting reactions or reducing the time required to conduct reactions.

SUMMARY

The present subject matter concerns a method including contacting a first component and a second component with a nanoporous structure and producing a product from a reaction of the first component with the second component. In one embodiment, the first and second components are incubated. The first and second components can be mixed together before contacting with the nanoporous structure, simultaneously, or after contacting with the nanoporous structure. The reaction product is produced under kinetic conditions that differ from those where the nanoporous structure is absent. For example, the product may be produced more rapidly in the presence of the nanoporous structure.

In one embodiment, a component is affixed to the nanoporous structure. The effective local concentration may be increased by the nanoporous structure. In one embodiment, a kinetic characteristic is adjusted prior to production of the reaction product. The kinetic characteristic may include a temperature, a concentration, a time period, a pH, a volume, a pressure, a diffusion rate, a material characteristic, an atmospheric humidity or a light exposure, among others. In one embodiment, the kinetic characteristic is measured after contacting the components with the nanoporous structure.

In one embodiment, a catalyst is used with the nanoporous structure. The catalyst may include an enzyme, a platinum powder, a metal and a metal complex. The enzyme may include a restriction enzyme, a ligase, a polymerase, a kinase, an amylase, an esterase, a dehydrogenase, a transferase, a synthetase, a synthase, a polymerase, a carboxylase, a reductase, a phosphorylase, a phosphotransferase, an aminotransferase, an oxidase, an isomerase, a deamidase, a fumarase, an anhydrase, a dismutase, a peptidase, an aldolase, an enolase, a luciferase, a urease, a galactosidase, a transcarbamylase, a glucosidase, a glucanase, or an endonuclease.

The catalyst may include cobalt, nickel, palladium, osmium or iridium. In addition, more than two components may be mixed and used with the nanoporous structure.

The first component may include an antibody, an antigen, a receptor, a substrate, a protein, an amino acid, a nucleic acid, a nucleotide, a lipid, a fatty acid, a carbohydrate, a hydrocarbon, a cofactor, a redox reagent, an acid, a base, a cellular fraction, a subcellular fraction, a virus sample, a fragment of a virus, a buffer, water or an organic solvent. In one embodiment, producing a product includes producing a modified nucleic acid, a nucleotide, an amplified nucleic acid fragment/sequence, a modified polypeptide, an amino acid, a cleavage product, an antibody/antigen complex, a ligand/receptor complex, an immunoassay product, a modified chemical, a sequencing fragment, a primary metabolite or a secondary metabolite.

In one embodiment, producing a cleavage product includes producing a nucleic acid fragment, a nucleotide, a polypeptide, an amino acid, a fatty acid, a carbohydrate, a polysaccharide, a simple sugar, a primary metabolite or a secondary metabolite. In one embodiment, producing product includes producing an amplified nucleic acid fragment and incubating includes applying a series of temperature changes suitable for sequence amplification.

Subsequent analysis of the product can be performed and in various embodiments, includes mass spectrometry, electrospray mass spectrometry, thin layer chromatography, electrophoresis, infrared spectroscopy, fluorescent spectroscopy, gas chromatography, atomic absorption, amino acid sequence analysis, nucleic sequence analysis, matrix assisted laser desorption/ionization (MALDI), surface enhanced laser desorption ionization (SELDI) or high performance liquid chromatography (HPLC). The product may also be stored, analyzed or used in a later reaction. Storing may include storing the product and nanoporous structure at room temperature, storing the nanoporous structure in a refrigerator, storing the nanoporous structure in a freezer, or storing the nanoporous structure in a pressurized or vacuum container. In various embodiments, the product is lyophilized, adsorbed or absorbed.

In one embodiment, the product is analyzed by separating, downstream processing, performing mass spectrometry (MS), performing MALDI-time of flight mass spectrometry (MALDI-TOF MS), performing SELDI MS, performing HPLC, performing nuclear magnetic resonance (NMR) analysis, performing synthesis or performing sequencing.

In one embodiment, the analyzing the product includes loading the nanoporous structure in a chromatography device, an electrophoresis based separation device, an electrochromatography separator device or a fraction collection device. In one embodiment, analyzing the product includes performing liquid chromatography, gas chromatography, column chromatography, thin layer chromatography, ion exchange chromatography, size exclusion chromatography, affinity chromatography, HPLC or affinity electrophoresis.

The present subject matter concerns a method including introducing a reaction mixture to a vessel, introducing one or more nanoporous structures to the vessel and circulating the reaction mixture within the vessel. The method may be used with nanoporous structures, membranes, beads or arrays. A differential migration process, including, for example, electrophoresis, may be performed on the product formed. The reaction mixture may include a first component and a second component in the vessel. In one embodiment, the first component is introduced to the vessel simultaneously with the second component.

The present subject matter concerns a system including a nanoporous structure, a reaction mixture distributor to establish contact between the reaction mixture and the nanoporous structure and an analysis tool to analyze a product produced by the reaction mixture. In one embodiment, the nanoporous structure includes a nanoporous membrane, strip, comb, sheet, filter, array or bead. In one embodiment, the reaction mixture distributor includes a 96 well plate, a spotting machine, a robotic microfluidic distribution device or a microjet printer. The analysis tool, in one embodiment, includes a mass spectrometer, an electrospray mass spectrometer, a thin layer chromatographer, an electrophoresis device, an HPLC device, an infrared spectroscope, a fluorescent spectroscope, a gas chromatographer, an atomic absorption device, an amino acid sequence analyzer or a nucleic sequence analyzer.

The present subject matter provides a method for modifying the kinetics of a reaction by providing one or more reaction components to form a reaction solution such that the reaction produces or result in one or more products. The reaction also has a known kinetic characteristic which is influenced or determined in part by at least one measurable kinetic factor. The reaction solution is contacted with a nanoporous membrane and incubated within the nanoporous membrane for a period of time sufficient to permit formation of the product or products. The product is thus obtained from the reaction under conditions resulting in a modification of at least one kinetic factor.

The component, or components, can include a catalyst. The catalyst can be, for example, an enzyme, platinum powder, rare metal complexes, and the like. Suitable enzymes include, for example, a restriction enzyme, a ligase, a polymerase, a kinase, an amylase, an esterase, a dehydrogenase, a transferase, a synthetase, a synthase, a polymerase, a carboxylase, a reductase, a phosphorylase, a phosphotransferase, an aminotransferase, an oxidase, an isomerase, a deamidase, a fumarase, an anhydrase, a dismutase, a peptidase, an aldolase, an enolase, a luciferase, a urease, a galactosidase, a transcarbamylase, a glucosidase, a glucanase, an endonuclease, an exonuclease, and the like. Other catalysts include, for example, platinum powder, metal complexes, cobalt, nickel, palladium, osmium, and iridium. The other component, or components, can be, for example, an antibody, an antigen, a receptor, a substrate, a protein, an amino acid, a nucleic acid, a nucleotide, a lipid, a fatty acid, a carbohydrate, a hydrocarbon, a cofactor, a redox reagent, an acid, a base, a cellular or subcellular fraction, a virus sample or fragment of a virus, a buffer, water, an organic solvent, and the like. The product can be, for example, a modified nucleic acid, a nucleotide, an amplified nucleic acid fragment/sequence, a modified polypeptide, an amino acid, a cleavage product, an antibody/antigen complex, a ligand/receptor complex, an immunoassay product, a modified chemical, a sequencing fragment, a primary metabolite or a secondary metabolite, and the like. Further, the cleavage product can be, for example, a nucleic acid fragment, a nucleotide, a polypeptide, an amino acid, a fatty acid, a carbohydrate, a polysaccharide, a simple sugar, a primary metabolite or a secondary metabolite, and the like. Where the product is an amplified nucleic acid fragment, the incubating step can be a series of temperature changes suitable for sequence amplification.

The modification to the kinetic factor can be a substantial quantitative change in the factor as compared to the reaction if conducted outside a nanoporous membrane. The kinetic factor can be, for example, temperature, concentration of a component, time, pH, volume, pressure, diffusion, a material characteristic, and the like. In cases wherein the kinetic factor is temperature, the modification can be a lower or higher temperature, or tolerance to a greater temperature range. In cases wherein the kinetic factor is time, the modification can be a shorter period of time, a longer period of time, or a greater tolerance to variabilities in incubation time. If the kinetic factor is concentration of a reaction component, the modification can be a lower concentration or a higher concentration, or a greater tolerance in the reaction to variability in concentration of one or all of the components. If the kinetic factor is volume, the modification can be a smaller volume or a larger volume, or a greater tolerance to variabilities in volume. Where the kinetic factor is pH, the modification can include a broader range of pH, a narrower range of pH, a higher pH, and a lower pH. If the kinetic factor is diffusion, the modification can be a shorter diffusion distance, a higher diffusion rate, a greater tolerance of the reaction for slow or variable diffusion rates, and the like. If the kinetic factor is a material characteristic, the modification is a greater adaptability or flexibility of the material characteristic as it interacts in the reaction.

The nanoporous membrane can include, for example, a microfilter, an ultrafilter, a gas separation membrane, a reverse osmosis membrane, a microlithographic pattern, a gel, a capillary, a thin layer substrate, a thin layer gel, a microchip, a depth filter, a particle bed, an array, and the like. The contacting step can occur after the combining step, or substantially simultaneously with the combining step. In various embodiments, the period of time can be less than 1 hour, or less than 20 minutes, or less than 1 minute. The incubating step can occur substantially simultaneously with the obtaining step. Alternatively, some or all steps can occur substantially simultaneously.

A further aspect of the present subject matter includes a nanoporous membrane reactor for conducting a reaction with modified kinetics. The device includes a reaction chamber with a nanoporous membrane network and can include one or more additional component. The additional component can include, for example, a product collector, an electrophoresis chamber, an electrochemical cell, a cuvette, a channel, a vent, a cross, a valve, a reservoir, an electrode, and the like.

Another aspect of the present subject matter includes a system for rapid, miniaturized reactions. The system has a nanoporous membrane network wherein a reaction is conducted, and generally includes an additional component. The additional component can be, for example, a nanoporous membrane and may additionally include, for example, a product collector, an electrophoresis chamber, an electrochemical cell, a cuvette, a channel, a vent, a cross, a valve, and the like. Another aspect of the subject matter includes a method of conducting a reaction for enhanced throughput. The method can include providing a reaction component to form a reaction solution, wherein the reaction produces one or more products. The reaction solution is contacted with a nanoporous membrane and incubated within the nanoporous membrane for a period of time sufficient to permit formation of the product within the nanoporous membrane. The nanoporous membrane containing the product is generally used in one or more subsequent steps. The subsequent steps can include, for example, storage, analysis, separation, transportation, clean-up, downstream processing, mass spectrometry (MS), MALDI-TOF MS, SELDI MS, nuclear magnetic resonance (NMR), synthesis, sequencing and a subsequent reaction. If the subsequent step is storage, the nanoporous membrane containing the product can be, for example, stored at room temperature, refrigerated, frozen, lyophilized, adsorbed, absorbed, stored in a pressurized container, and the like. If stored in a pressurized container, the container can contain one or more specific gases selected for stability or other purposes. If the subsequent step is analysis, the nanoporous membrane containing the product can be used, for example, as a loading device for chromatography, or in an electrophoresis based separation process, electrochromatography separation, post separation fraction collection, and the like. Chromatography or other separations can include, for example, electrophoresis, liquid chromatography, gas chromatography, column chromatography, thin layer chromatography, ion exchange chromatography, size exclusion chromatography, affinity chromatography, affinity electrophoresis, mass spectrometry (MS), NMR, MALDI-TOF MS, SELDI MS, HPLC, sequencing, and the like. The reaction solution can have a volume less than 1 microliter, less than 0.2 microliter, less than 0.1 microliters, or less than about 50 nanoliters.

The method of conducting a reaction for enhanced throughput can be adapted for high throughput screening of large numbers of products. The method can be applied, for example, to about 96, 384 or 1536 reactions or any other convenient number. A subsequent step can include multiplex screening of products of the reactions. A further aspect of the subject matter includes a kit for conducting a reaction for enhanced throughput. The kit can have a nanoporous membrane adapted to function as a reaction chamber for a reaction involving one or more reaction components. The kit may include at least one component of the reaction.

The present subject matter also includes a method of conducting a miniaturized, high throughput analysis of reaction products. This method can include forming a plurality of reaction solutions by providing, for each reaction solution, a component of a reaction. The reaction produces one or more products and the volume of the reaction solution, in one embodiment, is less than 5 µl. Each reaction solution or the plurality of reaction solutions can be contacted with a nanoporous membrane and incubated within the nanoporous membrane for a period of time sufficient to permit formation of the product within the nanoporous membrane. The nanoporous membrane containing the product can be used in at least one subsequent step. The reaction solution can have a volume less than 1.0 microliters, less than 0.2 microliters, less than 0.1 microliters, or less than about 50 nanoliters.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

FIG. 1 illustrates a nanoporous structure according to one embodiment of the present system.

FIG. 2 illustrates a nanoporous structure according to one embodiment of the present subject matter.

FIG. 3 illustrates a portion of a nanoporous structure according to one embodiment of the present subject matter.

DETAILED DESCRIPTION

Figure 4A:
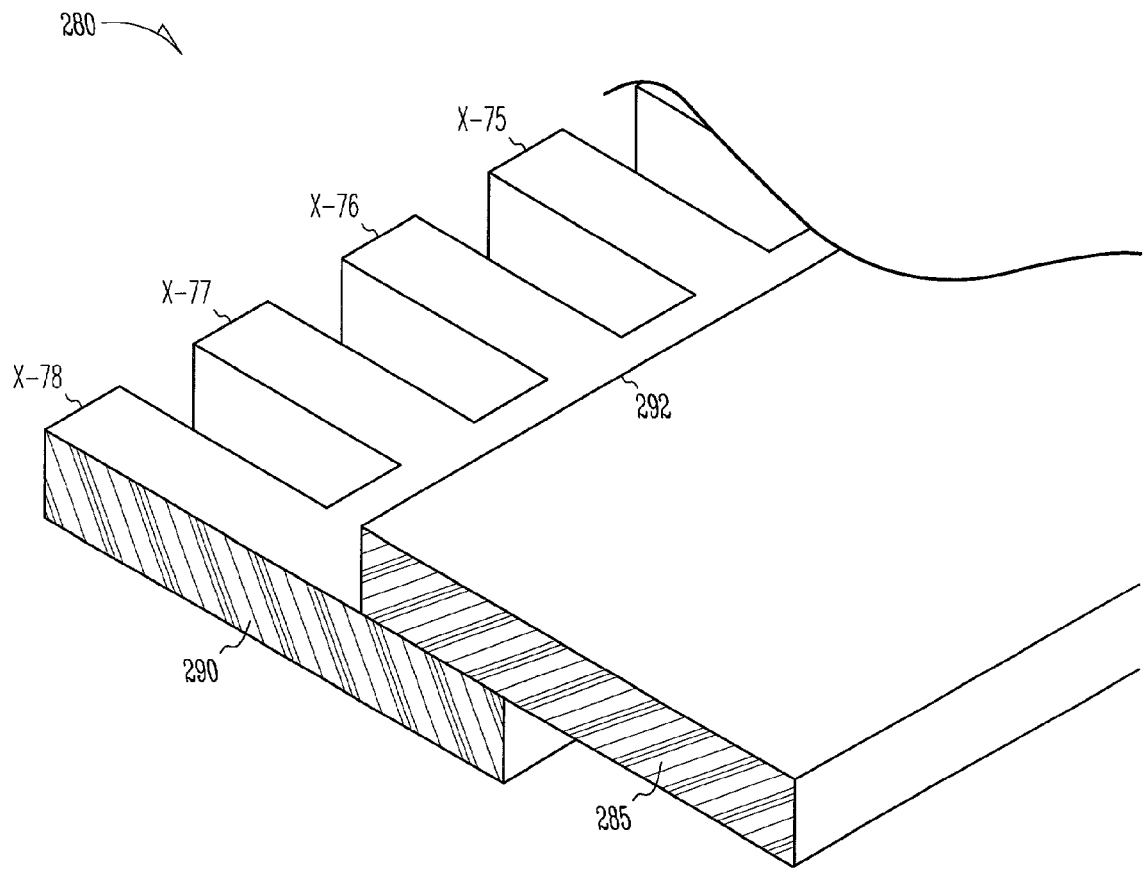
FIGS. 4A and 4B illustrate portions of a nanoporous structure according to one embodiment of the present subject matter.

In the following detailed description, reference is made to the accompanying drawings which form a part hereof, and in which is shown by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

This document describes, among other things, a method of performing nanoporous membrane mediated reactions. Existing reaction and experimental protocols may be operable with nanoporous membranes. For example, in one embodiment, a reaction that is not limited, or only partially limited, by diffusion distances results in enhanced kinetic characteristics. In addition, the miniaturization afforded by the present system, in terms of quantity of materials, volume and concentration of components, and size or dimension of equipment, allows, among other things, performing on-site and hand held reactions and analysis.

Scientific research seeks new methods, devices, and systems that are faster, smaller, less expensive, and easier to perform. In some cases, the speed with which a particular reaction goes to completion may be lengthy, and the time consumed in interfacing with downstream analytical devices and systems, performing analysis, and subsequently obtaining products or results may dissuade full and accurate analysis.

Kinetic factors may determine, or limit, the overall kinetic characteristic for a specific reaction. For example, the kinetic characteristic of a specific reaction may be affected by a rate of diffusion of certain components, concentrations and volumes of reagents, as well as specific pH, pressure, and temperature. In addition, kinetic factors contribute to the required incubation time for different reactions, limiting the speed with which products and results may be obtained. For example, with liquid based reactions, diffusion is a kinetic factor that can affect the characteristic for a particular reaction.

One embodiment of the present subject matter is operable using regular and microfabricated devices, thus leading to increased throughput, large scale application, and multiplexing. The nanoporous structure, or membrane, can function as a storage and clean-up medium, can be transported, and integrated with other procedures and equipment for subsequent downstream analysis.

The favorable conditions within nanoporous structures enhances the kinetic characteristics. Integrating reactions with the present subject matter can affect various kinetic factors, including reaction time, pH, pressure, temperature, concentration, volume, diffusion, and material characteristics. In one embodiment, the effect on the various kinetic factors can be tailored to affect performance of the reaction or analysis.

When applied to experimental protocols, the present subject matter provides enhanced kinetics, rapid miniaturization, and high throughput capability. Further, the subject matter can be interfaced with and applied to regular and microfabricated devices.

Embodiments of the present subject matter include a method for modifying the kinetics of a reaction as well as a device for conducting a reaction having modified kinetics. One embodiment provides a system for performing rapid miniaturized reactions which may be provided in kit form for conducting a reaction for enhanced throughput. One embodiment provides a method of conducting a miniaturized, high throughput analysis of reaction products, and the like.

Reactions performed on or within nanoporous membranes exhibit substantially improved kinetic characteristics. Such utility results from the favorable reaction conditions within the nanoporous network of the nanoporous structure, due, in part, to decreased diffusion distances within the network.

Embodiments of the subject matter provide a method for achieving enhanced reaction kinetics. According to one embodiment, components of the reaction are combined together to form a reaction mixture. In one embodiment, the reaction mixture includes only a single component. The reaction mixture is brought into contact with a nanoporous membrane. In one embodiment, the reaction mixture is incubated for a period of time. After the incubation period, a product results from the reaction with the product having been produced with an enhanced kinetic characteristic. The enhanced kinetic characteristic results from the reaction having an enhancement of at least one measurable kinetic factor. The resulting product formed in contact with the nanoporous structure can subsequently be used for analysis or reaction, thus enabling higher throughput. Alternatively, the product can be transported and stored within the membrane, and later subjected to further analysis or reaction.

Reactions can include chemical and biochemical reactions, chemical and biological interactions, as well as enzyme and other catalyst mediated processes. Reactions may produce individual or multiple products. Representative reactions include liquid based reactions, in which kinetic factors such as diffusion influences the overall kinetic characteristic. Examples of such reactions include restriction digests, PCRs, ligation, phosphorylation, other enzymatic reactions, non-enzymatic reactions, receptor-ligand binding, antibody-antigen binding, organic and inorganic chemical reactions, combinatorial chemical reactions, and the like. The aforementioned reactions can be integrated with a nanoporous structure, thus providing enhanced kinetics for the particular reaction. Integration with the present subject matter can also provide miniaturization, higher throughput, and allows interfacing with regular devices or microfabricated devices, and storage and transport capability.

One embodiment of the present subject matter includes one or more nanoporous membranes. The nanoporous membrane or structure may include a membrane network having pores, spaces, openings, channels, networks, reticula, and the like, with small diameters or volumes. In one embodiment the diameter of the pores, spaces, openings, channels, and the like is from about 1 nm or less to about 100 $\mu$m or more, or from about 10 nm to about 10 $\mu$m, or from about 100 nm to about 1 $\mu$m. Structures or membranes having nanoporous networks can be created by the user or obtained commercially in various types and makes, including, for example, microfilters, ultrafilters, gas separation filters or reverse osmosis filters. The nanoporous structure may be fabricated of, for example, non-plastic materials, paper, silica, silicon, glass, quartz polysulfones, polyvinylhalides, cellulosic materials, nylon, and the like.

A nanoporous structure composed of materials that are compatible with the particular type of reaction to be performed is selected. Compatibility with subsequent analytical steps or further reactions may also influence the choice of nanoporous structure. Compatibility can be determined by the properties of the reaction components and conditions. In some reactions, the nanoporous membrane can be treated or may require treatment prior to the reaction to protect the network or otherwise enhance utility. Examples of such a treatment include treating a nanoporous membrane with polymer molecules to prevent adsorption of particular components, such as polymerase enzymes in a PCR reaction. In PCR, nanoporous membranes also can be treated by various polymers including, for example, cellulose derivatives, polyethyleneoxide, polyethylene-glycol, polyvynilpyrrolidone, polyacrylamide, polyvynil-alcohol, dextrans, proteins, DNA, and complex carbohydrates.

This document refers to nanoporous membranes, however other structures are also contemplated. For example, the present subject matter also can include structures such as gels, capillaries, thin layer substrates (TLC), thin layer gels, microchips, depth filters, particle beds, arrays, beads and the like. Nanoporous networks, nanoporous membrane networks or nanoporous structures can be obtained commercially or created by the user. In one embodiment, the nanoporous structure is selected on the basis of compatibility with the components of the reaction.

Nanoporous structures of various physical dimensions and geometric orientations are contemplated. Nanoporous structures can be fashioned into a variety of sizes or shapes. For example, a nanoporous structure according to the present subject matter includes one or more nanoporous beads. For another example, a nanoporous membrane may be formed as a strip, a comb, a sheet, a filter, or various other configurations. Membranes may be in the form of a flat sheet or hollow fibers, with our without housings, modules or the like. In one embodiment, membrane mediated PCR, circular membranes having millimeter and sub-millimeter diameters are utilized in PCR wells. Similarly, 96, 384, or 1536 micro-well plates, typically used in high throughput analysis, may be used with one embodiment of the present subject matter. In one embodiment, a membrane may be in the shape of a strip or a comb, permitting loading and reaction of restriction digests of nucleic acids on the membrane, followed by integration of the membrane comb for loading samples in gel electrophoresis analysis.

Nanoporous membrane 280, as illustrated in FIG. 1, is operable with membrane mediated restriction digestion and electrophoresis. A user can integrate and perform multiple reactions, depending upon the number of tabs or teeth on the comb.

FIGS. 2 and 3 illustrate additional views of membrane 280 according to one embodiment. In FIG. 2, membrane 280 includes comb 290 and reinforcer 285. Reinforcer 285 includes alignment notches 295 at each end.

FIG. 3 illustrates a close view of membrane 280 according to one embodiment. Comb 290 includes a plurality of teeth, some of which are visible in the view shown and are denoted herein as X, X-1, X-2, X-3. In various embodiments, X is 96 or 100. In one embodiment X is an integer between 10 and 200 or between 50 and 150. In any particular analysis using membrane 280, a subset of the teeth may be used. Comb 290 is bonded to reinforcer 285, forming a laminate structure having visible joint line 292. Alignment notch 295 is visible in FIG. 3.

FIG. 4A illustrates a perspective view of a portion of membrane 280 when viewed in the direction of cut-line A—A shown in FIG. 3A. The bond line between comb 290 and reinforcer 285, and joint line 292, are visible in the figure. In FIG. 4A, teeth X-78, X-77, X-76 and X-75 of comb 290 are shown as rectangular teeth, however, other shapes and configurations are also contemplated. For example, the teeth of comb 290 may have a circular cross-section or include rounded ends in contrast to the square cuts shown. Comb 290 is illustrated as having teeth of uniform dimensions and features, however, alternative configurations are also contemplated. For example, the teeth may have progressively shorter dimensions or have larger area or include triangular, tapered, or pyramid shaped teeth.

Figure 4B:
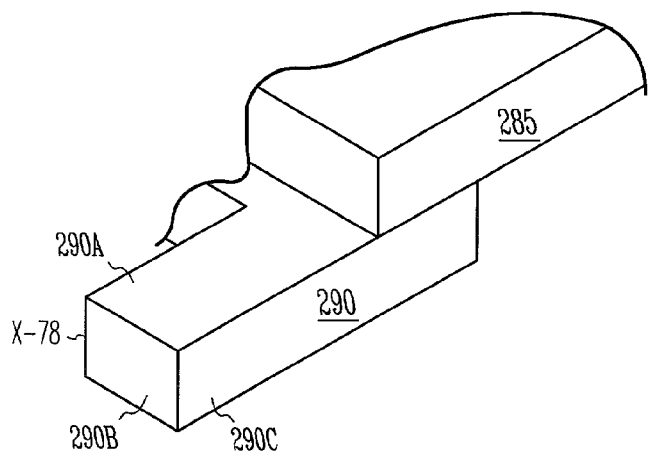

FIG. 4B illustrates a perspective view of representative tooth X-78 of comb 290 coupled to a portion of reinforcer 285. In one embodiment, the product or sample to be analyzed by electrophoresis is deposited or produced on one or more of surfaces 290A, 290B and 290C. In one embodiment, the product or sample is deposited onto membrane 280 robotically. On any particular comb 290, each tooth may carry a unique sample or some teeth may carry the same sample.

Figure 5:
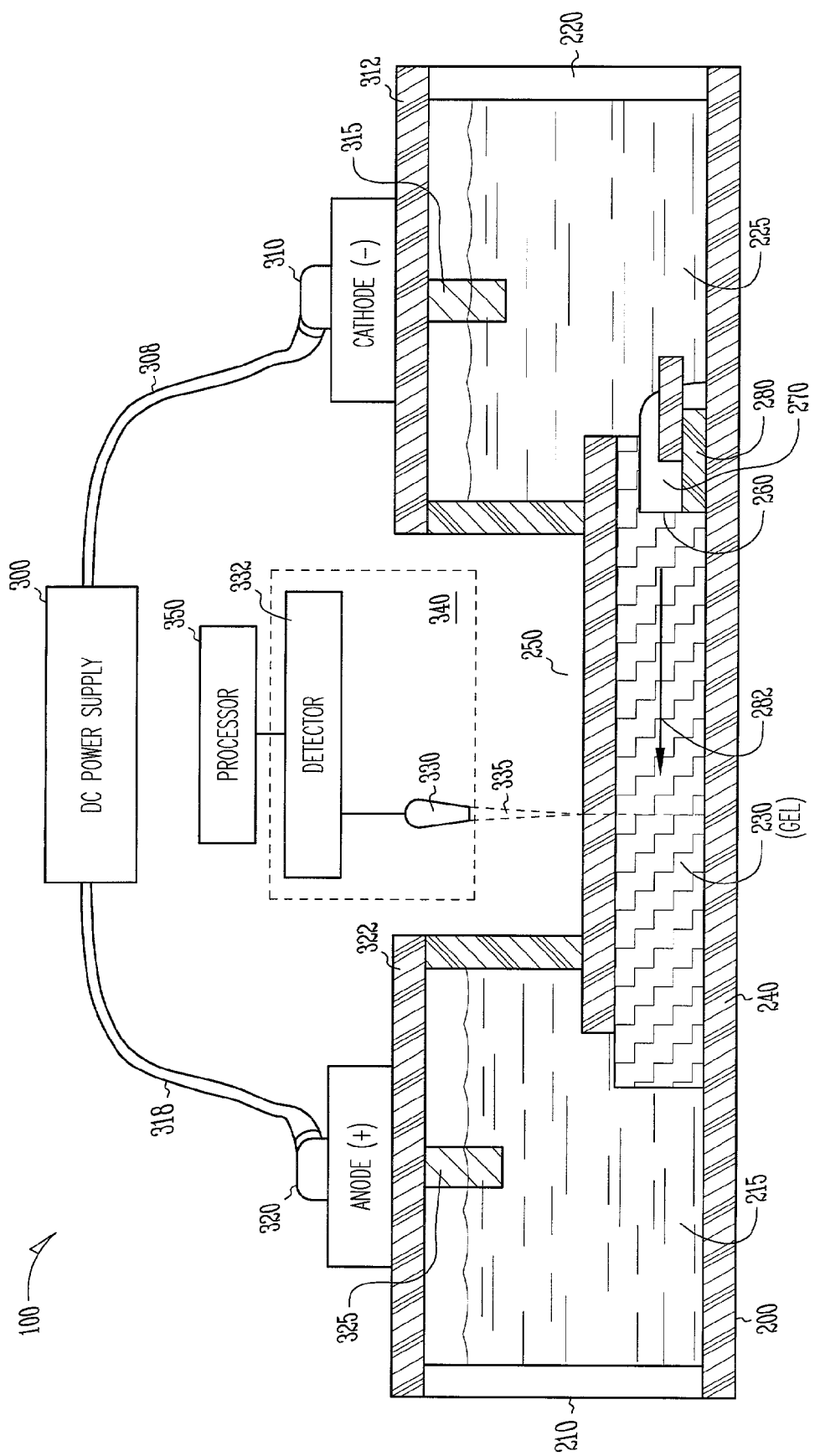
FIG. 5 illustrates an ultra thin layer gel electrophoresis system according to one embodiment of the present system.
Figure 6:
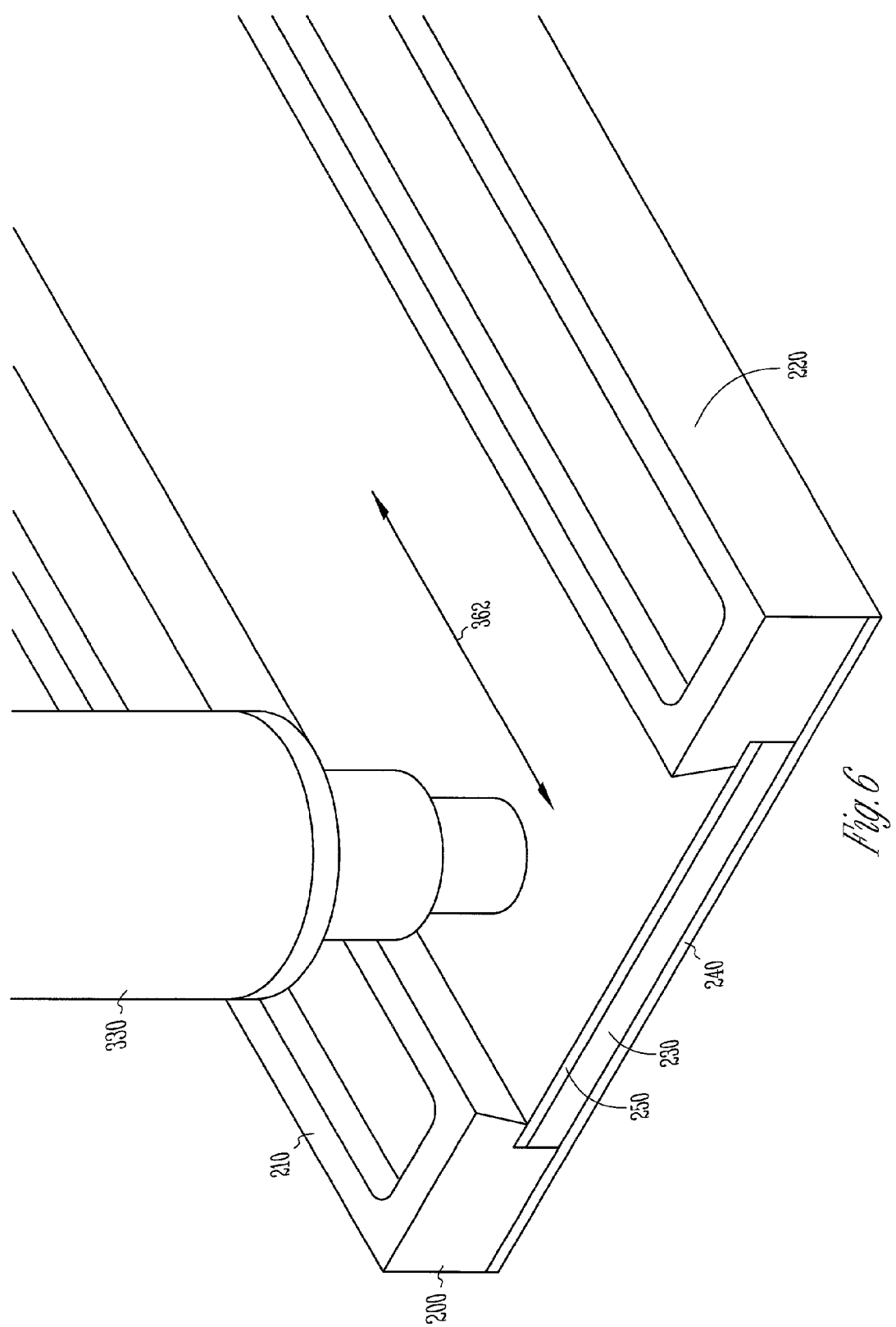
FIG. 6 illustrates another view of the system of FIG. 5.
Figure 7:
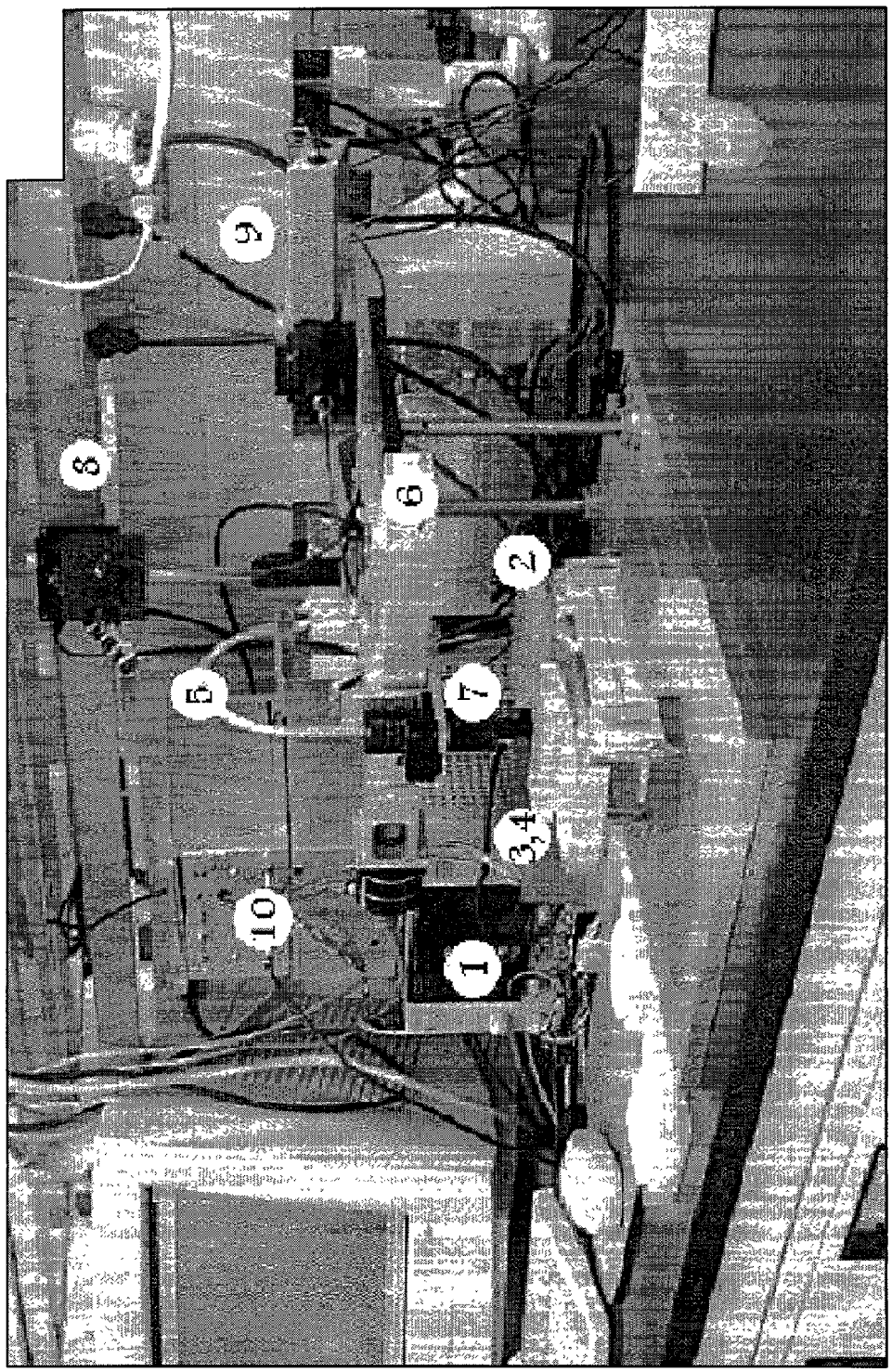
FIG. 7 illustrates a laboratory system for performing ultra thin layer gel electrophoresis according to one embodiment of the present system.

The nanoporous structure of the present system may be used with a variety of analysis tool and systems, including, for example, electrophoresis. A system for performing electrophoresis is illustrated in FIGS. 5, 6 and 7. Further description of thin film electrophoresis is found in U.S. patent application Ser. No. 10/047,461, entitled THIN FILM ELECTROPHORESIS APPARATUS AND METHOD, filed Jan. 14, 2002, invented by Andras Guttman, Bart Wanders and Phil Alei and assigned to Syngenta Participation AG, the specification of which is incorporated herein by reference.

FIG. 5 illustrates a sectional view of one embodiment of system 100 for conducting electrophoresis analysis in accordance with one embodiment of the present subject matter. Not shown in the figure are end caps for the reservoirs and the chamber and other structure.

In one embodiment, device 200 includes reservoir 210 and reservoir 220. Reservoirs 210 and 220 are coupled by a chamber which is bounded by upper plate 250 and lower plate 240. The chamber contains gel, or other separatory media, 230 and at least a portion of membrane 280. Reservoir 210 is capped with cover 322 and reservoir 220 is capped with cover 312. In one embodiment, cover 322 is coupled to anode 325 and cover 312 is coupled to cathode 315. In one embodiment, cover 322 is coupled to cathode 315 and cover 312 is coupled to anode 325. Anode 325 and cathode 315 are coupled to DC power supply 300 by leads 318 and 308, respectively. An electrical connection between anode 325 and lead 318 is established by connector 320. An electrical connection between cathode 315 and lead 308 is established by connector 310. It will be noted that anode 325 and cathode 315 may be positioned in a manner separately from covers 322 and 312, respectively. For example, anode 325 and cathode 315 may include flat conductors positioned within the respective reservoirs and bonded to lower plate 240.

In one embodiment, detection system 340 includes an optical detector 330 coupled to an optical densitometer 332. Densitometer 332 is coupled to processor 350. Other embodiments are also contemplated, such as for example, a fluorescence detection system. Processor 350, in one embodiment, provides data analysis.

Device 200 may be fabricated of translucent or opaque material including plastic, glass or other materials. In one embodiment, either upper plate 250 or lower plate 240 or both are fabricated of material compatible with detection system 340. In one embodiment, reservoir 210, reservoir 230, upper plate 250 and lower plate 240 are separately fabricated and bonded together in the manner illustrated to form leakproof joints.

In one embodiment, cover 322 and cover 312 protect the contents of reservoirs 210 and 220 from evaporation, foreign objects, and other contaminants. Covers 322 and 312 need not fit reservoirs 210 and 220, respectively, with a fluid tight seal.

In one embodiment, cover 322 and cover 312 carry electrical terminals. For example, anode 325 is coupled to cover 322 and cathode 315 is coupled to cover 312. With cover 322 in position on reservoir 210, anode 325 is in electrical contact with running buffer 215 and with cover 312 in position on reservoir 220, cathode 315 is in electrical contact with running buffer 225.

Separatory medium 230 occupies the chamber between upper plate 250 and lower plate 240. In one embodiment, upper plate 250 and lower plate 240 are substantially parallel and spaced apart by a distance of 190 microns. Distances greater than or less than 190 microns are also contemplated. In one embodiment, separatory medium 230 is formed in place by heating to a melting point and forcing into the space between upper plate 250 and lower plate 240.

Separatory medium 230 may include agarose or a gel known to one of skill in the art. In one embodiment, the separatory medium is pure agarose (in the range of, for example, 0.05–5% or 0.01 to 30%). In one embodiment, the separatory medium includes a composite. An example of a composite includes agarose and linear polyacrylamide (LPA) gel (with agarose in the range of, for example, 0.05–5%, or 0.01 to 30% and LPA in the range of, for example, 0.05–10%). In one embodiment, the separatory media is adapted to separate molecules in various molecular weight ranges. In various embodiments, the weight range is between 1,000 to 10,000,000 or 10,000 to 1,000,000,000 although other weight ranges are also contemplated.

Resolution of electrophoresis data is believed to be affected by temperature gradations across the separatory medium and the strength of the electric field through the medium. Here, the narrow dimensions of the chamber yields lower temperature variability, and thus, sharper bands of data with higher resolution. Higher temperatures cause the samples to move more rapidly, leading to more regularly shaped bands and less dispersion or blurred images. Thus, with less temperature gradient, the resolution improves since the bands remain sharp and narrow.

In addition, it is believed that the narrow dimensions of the chamber permit the use of a greater external electric field strength. For example, in one embodiment, the external voltage provided by supply 300 may be in the range of 50 to 100 volts per cm, with a typical value of 75 volts per cm. Thus, over a 10 cm distance, the supply voltage may be 1,000 volts. External cooling of device 200 may allow voltages greater than 100 volts per cm. For example, liquid cooling provided to upper plate 250 or lower plate 240 may allow use of a greater external field, and thus, higher resistance pathways and therefore, yield higher throughput. Liquid cooling may include water cooling or circulating a cooling agent or fluid in the proximity of the separatory medium. When using approximately 75 volts per cm to provide an external field, the run time for system 100 is typically 5 to 25 minutes in duration.

Electro osmotic forces (EOF) arising from application of the external electromagnetic field, may tend to move separatory medium 230 from within the chamber. In one embodiment, separatory medium 230 includes an additive that dynamically coats the interior surface of the chamber, thereby attenuating such electro osmotic forces. One such additive includes a polymer, such as polyvinylpiperidone (PVP), or dimethylacrylamide or other hydrophilic linear polymer.

In the absence of a coating on the interior of the chamber, the electrostatic charge of the fluid is generally positive fluid and the charge of the surface of the chamber is generally negative. Using a polymer coating yields a neutral surface and a neutral fluid, thus reducing electro osmotic forces.

Void 260 is formed in one end of separatory medium 230 located near reservoir 220 and at least partially within the space between upper plate 250 and lower plate 240. Void 260 is adapted to accept membrane 280 and a quantity of focusing water 270.

The constituent elements of the samples delivered to separatory medium 230 by membrane 280 travels in the direction indicated by arrow 282. The constituent elements are repelled by the cathode 315 end and attracted to anode 325 end.

FIG. 6 illustrates a perspective view of one embodiment of device 200 with cover 312 and cover 322 removed for the sake of clarity. In the embodiment illustrated, reservoir 210 and reservoir 220 are machined from a solid plastic block. Reservoir 210 and reservoir 220 are coupled to upper plate 250 and lower plate 240.

In the figure, optical densitometer detector 330 is positioned at a near end of separatory medium 230. Detector 330 is mounted on a track mechanism (not shown) and travels in the directions indicated by the arrowheads on line segment 362. In one embodiment, detector 330 includes a central optical fiber for transmitting a column of light and a plurality of sensor fibers distributed about the circumference of the central optical fiber for receiving reflected light. In cycling back and forth, detector 330 provides a signal based on the intensity of the bands generated by the constituent elements as each migrates through separatory medium 230. The output of detector 330 is processed by detector system 332 of FIG. 5 and further processed by processor 350, also of FIG. 5. In one embodiment, device 200 is mounted to a commercial stage apparatus and detector 330 is powered by a motorized carriage mechanism coupled to the stage.

In one embodiment of system 100, membrane 280 is installed in device 200 in such a manner that the thicker portion of comb 290 and reinforcer 285 is positioned under reservoir 220 and a portion of the teeth of comb 290 are inserted within the space between upper plate 250 and lower plate 240. Other embodiments are also contemplated, such as for example, insertion of membrane 280 to a greater or lesser depth.

For example, FIG. 7 illustrates one embodiment of a system that integrates restriction digestion with gel electrophoresis, where the samples are digested and analyzed on a gel in a time period that may be measured in seconds or minutes. The system includes high voltage (HV) power supply 1, platinum electrodes 2, ultra thin layer separation platform 3 with built in buffer reservoirs 4 and a fiber optic bundle based laser induced fluorescence detection system (5–9). Lens set 7 is connected to the illumination/detection system via fiber optic bundle 5 and scans across the gel by means of translation stage 6. A 532 nm frequency doubled Nd-YAG laser excitation source 8 is connected to the central excitation fiber and avalanche photodiode detector 9 is connected to the surrounding collecting fibers of the fiber optic bundle. Interface electronics 10 is adapted to digitize the analog output of the detector and to connect the system to a personal computer (PC). The horizontal separation platform is placed on a positional heat sink that holds the gel filled cassette. This heat sink also eliminates local heat spots generated by separation irregularities caused by uneven heat dissipation.

Figure 8:
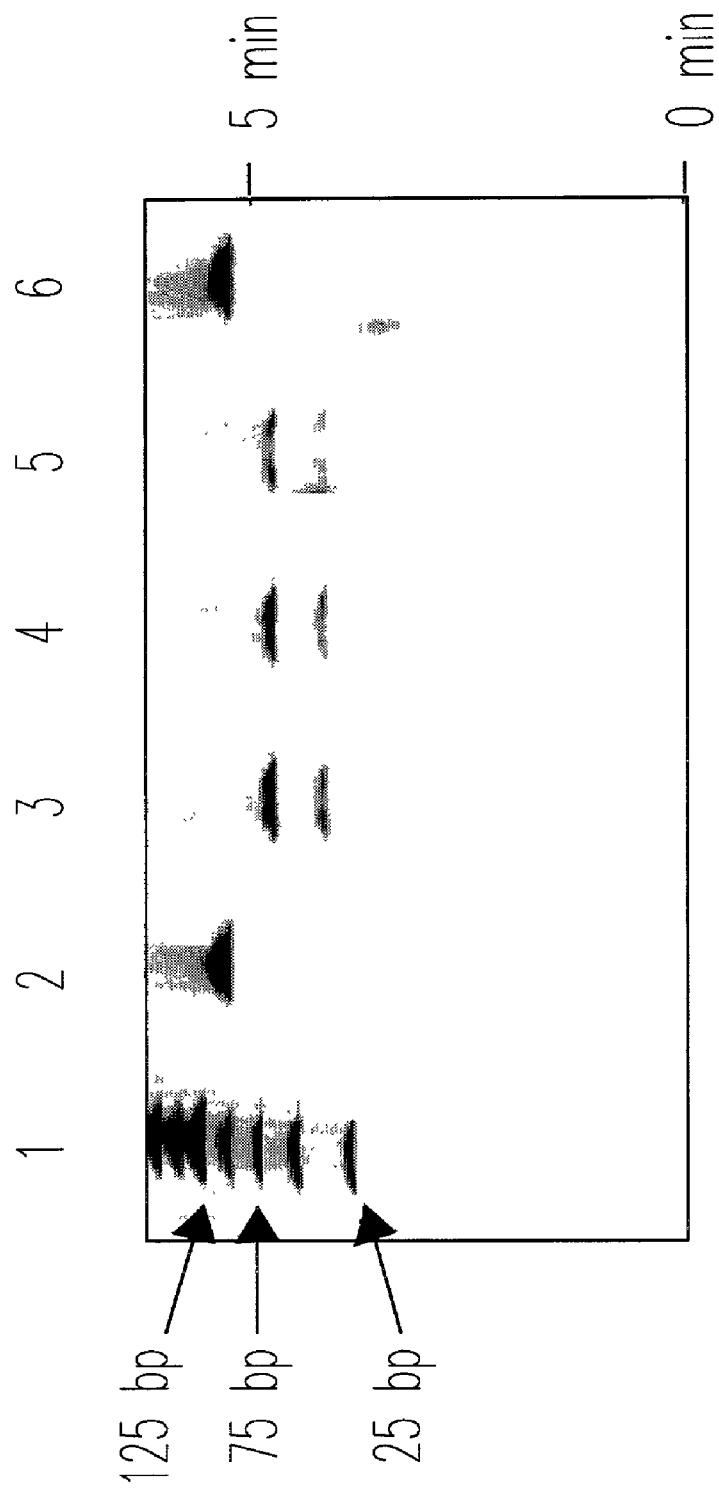
FIG. 8 illustrates an ultra thin layer gel electrophoresis analysis of samples that were digested on a comb as illustrated in FIG. 1.

FIG. 8 shows ultra thin layer gel electrophoresis analysis of samples that were digested on a comb as illustrated in FIG. 1. FIG. 8 illustrates a nucleic acid sizing ladder along with digested and undigested samples. In one embodiment, after completing the reactions on the comb, the membrane comb containing the reaction mixture/product is transported and directly integrated with the electrophoresis apparatus. Alternatively, the mixture, or product-containing comb is stored for later processing or analysis.

High throughput reactions, such as, for example, drug screening, DNA sequencing, protein digestion, carbohydrate profiling and sequencing, organic synthesis, antibody-antigen binding and like protocols also may be integrated with the present subject matter. Membranes or structures can be fashioned to integrate with the systems for the above-mentioned protocols and the like. Further embodiments permit the membrane (or portions of the membrane) to be integrated with regular or microfabricated devices, such as silicon or glass microchips.

In addition, other devices may also be interfaced or integrated for use with the present subject matter. Examples include microlithographic patterns, nanocapillary computer chips (for integration with computers), gel matrices (for integration with subsequent liquid based analysis—for example, add as nanoporous slurry to HPLC), glass matrices, plastic matrices and the like.

According to some embodiments of the present subject matter, a reaction mixture is contacted with the nanoporous network. In one embodiment the reaction mixture includes one component. Examples of one-component reactions include decay and transformation reactions. In these one-component reactions, the reaction mixture containing the single component is added to the network.

In other embodiments, the reaction mixture includes a combination of components. For example, at least one component may be combined with a second component. However, reactions may entail many components or a number of sequentially added components. Since the methods and devices of the subject matter can be applied to reactions in which shortened diffusion distances or enhancements of other kinetic factors can be beneficial, the scope of the present subject matter is not necessarily limited to a particular reaction or class of reactions.

In some embodiments, components may be combined, for example, in a test tube, or microcentrifuge tube, prior to contacting with the surface of the nanoporous network or structure. Components may be spotted onto a surface, such as a paraffin film, and combined thereon prior to transfer to the network. In one embodiment, a user directly spots the components of the reaction onto the surface of the nanoporous structure or network. Where more than one component is used, the user may combine the components on the surface of the network by directly spot-loading the components thereon. Other embodiments employ a hybrid approach to contacting the components onto the nanoporous network. For example, some components may be combined prior to contact with the surface of the network (such as in a microcentrifuge tube) while others are combined directly on the surface of the network and the components combined outside of the network are transferred to the surface of the network and combined with the previously added components.

A component can include a substance present in a reaction. The component, or components, (including a first or second component), may include, for example, an antibody, an antigen, a receptor, a substrate, a protein, an amino acid, a nucleic acid, a nucleotide, a lipid, a fatty acid, a carbohydrate, a hydrocarbon, a cofactor, a redox reagent, an acid, a base, a cellular or subcellular fraction, a virus sample or fragment of a virus, a buffer, water, an organic solvent and the like.

The first or second component may also include a catalyst. Examples of catalysts are metal complexes (including rare metal complexes), enzymes, metal powders such as platinum powder and the like. Rare metal complexes include cobalt, nickel, palladium, osmium, iridium and the like. Enzyme catalysts can include, for example, restriction enzymes, ligases, polymerases, kinases, amylase, esterase, dehydrogenase, transferase, synthetase, synthase, polymerase, carboxylase, reductase, phosphorylase, phosphotransferase, aminotransferase, oxidase, isomerase, deamidase, fumarase, anhydrase, dismutase, peptidase, aldolase, enolase, luciferase, urease, galactosidase, transcarbamylase, glucosidase, glucanase, endonuclease, exonuclease and the like.

In embodiments using nanoporous membrane mediated PCR, synthase or restriction digestion, components can include nucleic acid or nucleotides. These components may also be utilized in other nanoporous network mediated reaction protocols, such as sequencing reactions. For example, in one embodiment, one component includes a nucleic acid molecule, a second component includes a restriction enzyme catalyst, and another component includes a buffer. The nucleic acid, the enzyme, and the buffer may be combined in a microcentrifuge tube, then transferred to a nanoporous network or structure.

In one embodiment, one or more of the components are spotted directly onto the surface of the nanoporous network. Spotting of components onto a nanoporous network can be automated, as with robotic microfluidic devices, microjet printers, and the like, or the spotting process can be performed manually. At the conclusion of the reaction, the nanoporous structure may be integrated with an agarose gel, a microchip or a microcapillary for electrophoretic analysis. In one embodiment, the network is integrated as part of an analysis system where the components are added to the nanoporous network or structure in situ and thus avoid transportation.

The components may be combined either directly on the surface of the nanoporous membrane network or prior to contacting with the surface of the network. The reaction components come into contact with the nanoporous membrane network in order to react within the environment of the nanoporous matrix of the particular network. Contacting the reaction mixture with a nanoporous membrane network allows a reaction to proceed with enhanced kinetics.

In one embodiment, the reaction mixture is incubated within the nanoporous structure while subjected to predetermined conditions for a period of time sufficient to permit formation of the product or completion of the desired reaction. The incubation period may be simultaneous with contacting the components with the membrane, providing substantially a zero time of required incubation. In various embodiments the incubation period can be 0–10 s, 15–30 s, 45–90 s or more. In other embodiments the period can be 1–3 min, 5–10 min, 15–30 min or more. Depending on the nature of a given reaction, the incubation period may be some other period of time, and may represent an enhancement in reaction time as compared to the same reaction if conducted outside a nanoporous environment or in a non-nanoporous environment. In various embodiments, the period of time for incubation is substantially simultaneous with the combining and contacting of components on the surface of the nanoporous structure or membrane.

The incubation period may include addition, or removal, of various components in a sequential manner. As another example, the incubation period may include a series of repetitive steps such as a series of temperature changes in a nucleic acid amplification of a nucleic acid sequence. Incubation conditions may include a certain temperature, pressure, pH, humidity, light, and the like, or a changing or repeating series of temperatures, pressures, pHs, humidities, light wavelengths or intensities or the like.

At the conclusion of the incubation period, a product is obtained with an enhanced kinetic characteristic. Different products may result from the reactions including, for example, a modified nucleic acid, a nucleotide, an amplified nucleic acid fragment or sequence, a modified polypeptide, an amino acid, a cleavage product, an antibody-antigen complex, a ligand-receptor complex, an immunoassay product, a modified chemical, a sequencing fragment, a primary metabolite or a secondary metabolite, and the like.

The product of a cleavage reaction can include, for example, a nucleic acid fragment or a nucleotide, a polypeptide or an amino acid, a fatty acid, a polysaccharide or a simple sugar, fragments of the foregoing types of molecules, a primary metabolite or a secondary metabolite, and the like.

The kinetic characteristic of the reaction which results in the product is modified in the nanoporous structure. The kinetic characteristic of a reaction may be determined by one or more quantitative kinetic factors that contribute to a particular kinetic characteristic. Embodiments of the present subject matter which includes nanoporous membrane mediated reactions, provide for quantitative change in the kinetic factors as compared to the reaction if conducted outside of a nanoporous membrane. Examples of kinetic factors capable of modification or enhancement include time, temperature, pH, volume, concentration, pressure, material characteristic, diffusion, and the like.

In one embodiment, the time for a reaction to proceed to product is decreased. The amount of the decrease in time is relative to the specific reaction. In various embodiments, the reduction in reaction time is between 0 seconds and several hours. In one embodiment, the reduction in reaction time is measured in days. For example, a typical restriction digestion of DNA can take hours or even overnight, but in some embodiments of the present subject matter, restriction digestion on a membrane is accomplished in minutes or seconds.

Temperature is a kinetic factor that is affected by embodiments of the present subject matter. For some membrane-mediated reactions, the temperature used for a successful reaction is decreased. Under non-nanoporous conditions, a reaction may proceed at temperatures above a particular temperature, however, when conducted using one embodiment of the present subject matter, the reaction proceeds at a lower temperature. In various embodiments, the temperature for reaction is reduced by 1° or less, 3–5°, 7–10°, 15°, 20°, 25°, 30°, 65° C., or more degrees. For example, in one embodiment, the range of temperatures may be between room temperature and 65° C. with many reactions occurring at 37° C.

A lower reaction temperature may prove advantageous for certain applications. For example, a reaction that would typically require an incubation temperature of 65° may instead be conducted at room temperature using the present subject matter. As another example, the present subject matter may allow performing a reaction in an environment at a particular temperature. For example, the present subject matter may allow a reaction to proceed at 4°, thus permitting a series of steps to be performed that would otherwise be temperature barred. Various embodiments of the present subject matter are operable across a broad range of temperatures.

One embodiment of the present subject matter allows reactions to be performed with greater temperature consistency. In one embodiment, the nanoporous membrane network provides improved temperature distribution and equilibration due to the shorter distances within the network or structure (no diffusion limitation).

In some embodiments, the required pH for a reaction is lower than the required pH when the reaction is conducted outside of a nanoporous network. In other embodiments, the pH is higher. Further, in some embodiments, the range of acceptable pH for a reaction is broader. The range of pH is narrower in other embodiments.

One embodiment of the present subject matter enhances volume requirements for some reactions. In various embodiments, the volume of reaction mixture and components is decreased. Use of smaller volumes may be beneficial because of the reduction in consumption of component, reagent, or product, and the resultant production of waste. Less waste and consumption further contributes to more cost efficient reactions. In one embodiment of the present subject matter, the volume for a reaction is approximately 0.001 $\mu l$, 0.005 $\mu l$, or 0.01 $\mu l$ or less, and 5 $\mu l$, or more or between about 0.03 $\mu l$ and 3 $\mu l$ or between about 0.1 $\mu l$ and 1.0 $\mu l$.

The present subject matter is also operable with large-scale reactions having large volumes. For example, one embodiment provides for volume quantities in the range of liters or greater. The nanoporous structures or hollow fiber membranes of one embodiment provides enormous surface area in a relatively small volume. Where a large quantity of product is sought, with rapid or otherwise kinetically enhanced reaction characteristics, one embodiment of the present subject matter contemplates use of hollow fiber membrane networks as a substrate for such reactions.

The minimum concentration of components is reduced in one embodiment of the present subject matter. Components are channeled into close spatial proximity allowing interaction and reaction. In one embodiment, the minimum concentration can be reduced by 1000-fold, or more and in other embodiments the concentration can be reduced by, for example, 300-fold, 100-fold, 30-fold, 10-fold, 3-fold, or 2-fold. Reductions in minimum concentrations may be advantageous in reducing reagent costs, particularly in the cases of expensive enzymes and other catalysts.

Figure 9A:
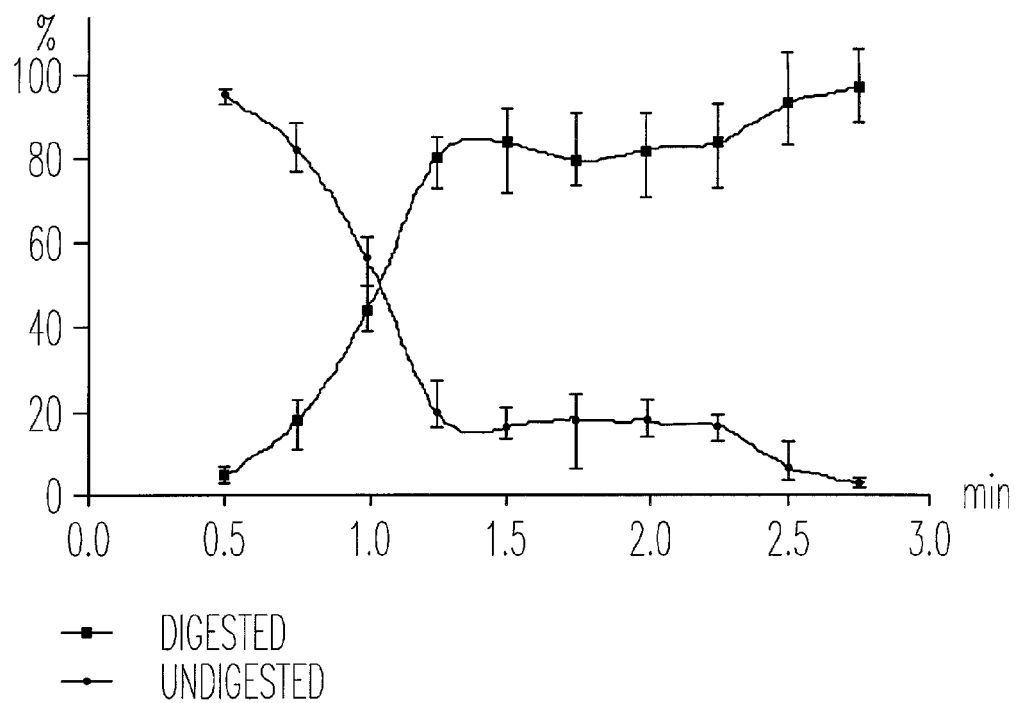
FIG. 9A illustrates the percentage amounts of cleaved and uncleaved fragments as a function of the digestion time
Figure 9B:
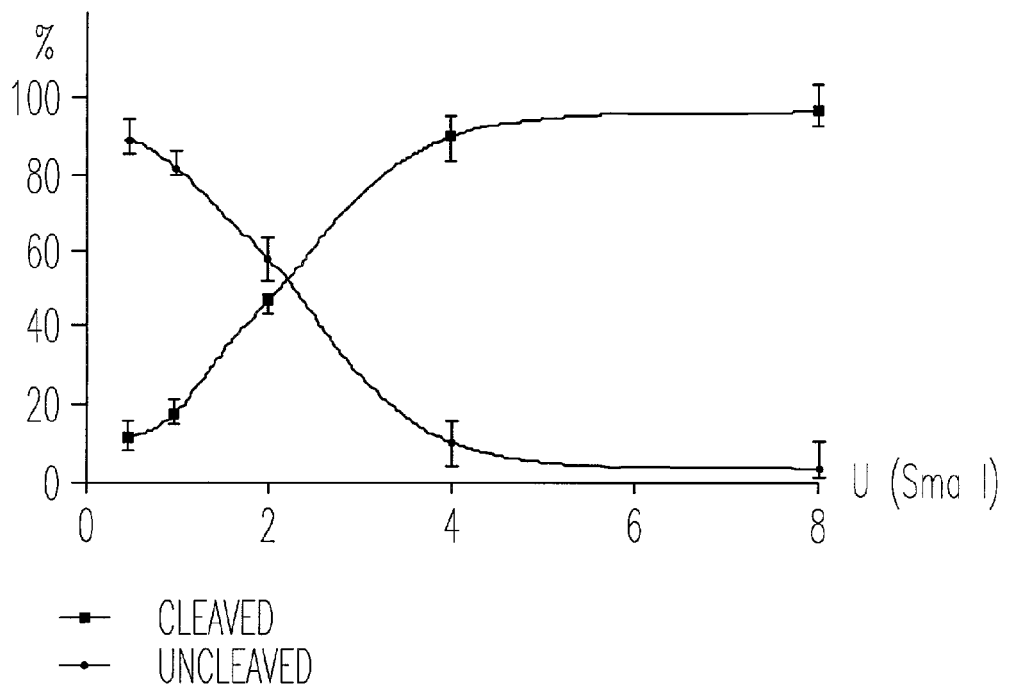
FIG. 9B illustrates the enzyme of FIG. 9A and shows concentration dependence of the membrane mediated digestion process.

For example, FIG. 9B depicts the enzyme concentration dependence of the membrane mediated digestion process. The curve in the figure shows that substantially complete digestion occurs at the same, or a reduced, concentration as compared to reactions conducted in a non-nanoporous environment. Thus, concentration is another example of a kinetic factor that can be enhanced using one embodiment of the present system.

In one embodiment, the pressure for performing a reaction is higher and in other embodiments, the pressure is lower than that of a reaction in a non-nanoporous environment. Thus, the present subject matter allows conducting reactions at atmospheric conditions at various ambient conditions of pressure, temperature or other kinetic factors. For example, embodiments of the present subject matter permit conducting analysis in high-pressure environments (such as deep sea studies), or in low pressure environments (such as space, very high altitude) as well as environments having non-standard temperature and pressure.

Diffusion limits the kinetics of some liquid based reactions. Diffusion as a limiting factor on overall reaction kinetics can be reduced by the present subject matter. The smaller distances and diameters of the nanoporous structure leads to reduced diffusion distances, and thus, the time for two reaction components to contact each other or collide is also reduced. Furthermore, the frequency of such contacts is increased. The result is enhanced kinetics for a particular reaction. Since higher temperatures or higher component concentrations in certain reactions can, in part, compensate for large diffusion distances, a reaction employing reduced diffusion distances can proceed at correspondingly lower temperatures or lower concentrations of components.

In some embodiments, the subject matter provides a nanoporous reactor for conducting a reaction with modified kinetics. The nanoporous reactor has a reaction chamber incorporating a nanoporous membrane or structure. In some embodiments, the nanoporous membrane itself is the reaction chamber and defines the physical boundaries of the reaction chamber. The device can also have at least one additional component, which can include, for example, a product collector, an electrophoresis chamber, an electrochemical cell, a cuvette, a channel, a vent, a cross, a valve, reagent reservoir, a sample reservoir, a buffer reservoir, electrodes and the like. The aforementioned components are commercially available and integration of such components with the nanoporous reaction chamber can be achieved and implemented according to the specific application.

One embodiment includes a system for rapid, miniaturized reactions. The system utilizes a nanoporous membrane and additionally include a product collector, an electrophoresis chamber, an electrochemical cell, a cuvette, a channel, a vent, a cross, a valve or the like.

One embodiment of the subject matter includes a method for conducting an enhanced throughput reaction. The enhancements provided by the present subject matter allow high throughput experimentation and analysis. Individual reactions are performed faster, increasing the rate of product yield and analysis. The reaction product containing nanoporous membrane can be stored, transported and interfaced for further downstream processing. A reaction solution/mixture including at least one component is reacted. Alternatively, the reaction solution/mixture may include a combination of at least a first and at least a second component. As discussed above, the reaction solution is added to the nanoporous membrane and incubated for a period of time sufficient to permit formation of the product within the network of the membrane. As set forth in detail below, the nanoporous membrane containing the product is then used in at least one additional step.

The DNA samples, enzyme and buffers are spot-loaded onto a tab or tooth of a membrane comb, as shown in the sample comb of FIG. 1. The digestions take place in a period of time measured in minutes. In FIG. 9A, a 101 bp PCR product was completely digested in 1.25 minutes at room temperature. In one embodiment, the membrane comb is then directly interfaced as a loading device for the subsequent gel electrophoresis. Using a system similar to that in FIG. 7, a large number of samples are analyzed in a short period of time. In one embodiment, the product containing membrane or structure is stored. The membrane may be stored at room temperature, in a freezer, a refrigerator, a dessicator, in a pressurized container or under specific gases. In addition, the product may be lyophilized or adsorbed.

In one embodiment, the reaction mixture and product containing nanoporous membrane functions as a storage and cleanup medium. The membrane can be frozen, refrigerated, lyophilized, or stored under pressurized specific gases. Favorable conditions within the network contribute to less damage to the product due to expansion, freezer damage, protection from contamination, and the like.

One embodiment of the present subject matter includes conducting subsequent analysis of the product. For example, the nanoporous network can be used as a loading device for chromatography, electrophoresis-based separations, electrochromatography separation, post separation fraction collection, PCR, spectrophotometry, radiometry, MALDI-TOF MS, SELDI MS, electrospray, ion-spray MS, HPLC, and the like. Mass spectrometry chromatography may include gas and liquid chromatography, thin layer chromatography, ion exchange chromatography, size exclusion chromatography, affinity chromatography, affinity electrophoresis, other MS types, surface plasmon resonance spectroscopy and the like. Subsequent analysis may also include performing electrospray mass spectrometry, thin layer chromatography, electrophoresis, infrared spectroscopy, fluorescent spectroscopy, gas chromatography, atomic absorption, amino acid sequence analysis, nucleic acid sequence analysis and others.

The products within the networks can be analyzed immediately after production or analyzed after a period of storage. Analysis may include, chromatography, electrophoresis, liquid chromatography, gas chromatography, column chromatography, mass spectrometry, MALDI-TOF MS, NMR and the like. Subsequent reactions may also be performed, such as PCR, digestion with other enzymes, labeling (fluorophore), ligation, derivatization, and the like.

Integration of a nanoporous membrane with other analysis systems allows enhanced high throughput reactions using reduced solution volumes. For example, in some embodiments the required reaction volume is less than 3 microliters. In other embodiments the required volume is less than 2 microliters. One embodiment of the subject matter uses a volume less than 1 microliter. In one embodiment, the reaction volume is less than 0.1 microliters.

Embodiments for conducting reactions with enhanced throughput can be interfaced with 96, 384 and 1536-well reaction plates, and the like. Further, integrating reaction well plates and the like with embodiments of the present subject matter permits multiplex screening reactions.

Another embodiment of the subject matter includes a kit for conducting reactions with enhanced throughput. In one embodiment, the kit includes a nanoporous membrane adapted to function as the reaction chamber for reactions with one or more components. In one embodiment, the kit includes a nanoporous membrane reaction chamber and one reaction component. The remaining component, or components, can be included in the kit or can be provided separate from the kit. For example the kit may include the membrane and a particular restriction enzyme. The user provides the remaining components, the strand of nucleic acid that is to be analyzed and a buffer. Conversely, the kit may include the network and a catalyst, an antibody, or enzymes and reaction components.

One embodiment of the present subject matter includes a method for miniaturized, high throughput analysis of reaction products. The user provides or creates a plurality of reaction solutions or mixtures. A plurality may be an amount greater than one and in various embodiments it is at least 96, 384, or 1536, to allow use with multi-well plate reactors and analyzers. The reaction solutions may contain one component or a combination of more than one component. The solutions are contacted with the structure or membrane as discussed above, including by directly spotting the components or the reaction solution onto the membrane. In one embodiment, the reaction solutions or mixtures are incubated for a period of time sufficient to permit formation of a reaction product or products within the membrane. The membrane, along with the reaction product, may be used in a further procedure. For example, the membrane and reaction product may be stored or analyzed subsequently.

EXAMPLES AND APPLICATIONS

The following sections describe specific examples of methods and systems operable using the present subject matter. These examples are not to be taken as limitations but rather as representative particular applications.

Chemicals for PCR and Restriction Digestion

In the experiments described in Examples 1 and 2 below, a 1% low electroendosmotic (EEO) agarose gel $-m_r=0.1$ (Sigma, of St Louis, Mo.) was dissolved in 45 mM Tris, 45 mM boric acid, 1 mM EDTA_Na$_2$ buffer, pH 8.3 (referred to 0.5_TBE). Tris, boric acid and EDTA Na$_2$ were obtained from ICN (Costa Mesa, Calif.), in electrophoresis grade. The linear polyacrylamide (LPA, M$_r$700,000–1,000,000) was obtained from Polysciences (Warrington, Pa.). The ethidium bromide fluorescent dye was obtained from Sigma (St Louis, Mo.). The 25 and the 100 bp DNA ladder, the Hind III and Hae III restriction endonucleases with the REACT 2 buffer were obtained from Life Technologies (Gaithersburg, Md.). SmaI, SacI, BamHI, BstEII restriction enzymes with NEBuffer 1-4 and the pUC 19 DNA were obtained from New England Biolabs (Beverly, Mass.). Oligonucleotide primers were obtained from Sigma Genosys. dNTP solution PLATINUM Taq DNA polymerase with the 10$_{13}$ buffer and the 50 mM MgCl$_2$ were obtained from Life Technologies (Gaithersburg, Md.). Gel loading combs were obtained from Genetic Biosystems (San Diego, Calif.). Nanoporous membranes, or structures, were made of and nitrocellulose, cellulose acetate, polyethersulfone, polysulfones, and mixtures of these ingredients.

Example 1

PCR

Membrane mediated PCR based amplification of polynucleotides was accomplished on a small pore size nanofibrous membrane. Prior to use, the membrane was treated by polymer molecules including cellulose derivatives, polyethyleneoxide, polyethyleneglycol, polyvynil-pyrrolidone, polyacrylamide, polyvinylalcohol, dextrans, proteins (such as BSA), DNA, and complex carbohydrates to avoid adsorption of the polymerase enzyme or other particular components of the reaction mixture to the large surface area. A 101 bp fragment of the pUC 19 cloning vector (template DNA) was amplified. The reaction mixture contained 200 µM dNTP, 1.5 mM MgCl$_2$, 0.05 U/µl Taq polymerase, 0.5 ng/µl pUC 19 DNA and 0.5 µm of each primers (forward primer: 5' GTA AAA CGA CGG CCA GTG 3' (SEQ ID NO:1), reverse primer: 5 'GGA AAC AGC TAT GAC CAT G 3' (SEQ ID NO:2)) in a total volume of 10 µl. The pUC 19 template was mixed with the primers, the Taq polymerase enzyme, relevant nucleotide triphosphates and buffer components and delivered onto the surface of a pretreated nanoporous structure in the form of a membrane.

The amplification process took place within the capillary channel network of the nanoporous membrane. In one embodiment, thermocycling is initiated, at 95° C. for 2 minutes, to denature the double stranded DNA template and followed by 30 cycles of 0.5 minutes of denaturation at 94° C., 0.5 minutes of annealing at 60° C. and 0.5 minutes of extension at 72° C. A last extension at 72° C. for 3 minutes is followed by cooling the samples to 4° C.

After thermal cycling of the temperatures for the particular time periods, the amplified fragments were further processed on the membrane or analyzed. The reaction mixture containing membrane was also used as a vehicle for downstream processing, such as further reactions and electrophoresis based analysis. This method reduced reagent consumption (submicroliter) and provided rapid amplification kinetics, due to favorable reaction conditions in the capillary network of the nanoporous membrane.

Existing PCR protocols can be applied and miniaturized to nanoporous membrane mediated polynucleotide amplification. In addition, membrane mediated amplification can be performed on small membrane pieces (mm and sub-mm diameter) that can be interfaced with regular and microfabricated separation devices. Thus, large scale application and multiplexing is supported.

Embodiments of the subject matter thus provide the capability of using submicroliter amounts of reagents, thus reducing sample, primer and enzyme consumption, decreasing the amount of chemical/biochemical and container (plastic tubes) waste as well as reducing the cost of analysis.

Due to the reduced reaction volume in the capillary network of the nanoporous membrane, the reaction was accomplished more rapidly (i.e. minutes) due, at least in part, to diffusion not limiting the reaction. Reaction mixture containing nanoporous membranes can be stored for future analysis and used as a vehicle for transportation to different locations for downstream processing and analysis. Laboratory space occupied by the PCR amplification is reduced, also allowing the implementation of handheld devices (on-site PCR and analysis). These embodiments of the subject matter also provide for application of the reaction mixture containing membranes to various regular and microfabricated separation devices.

Figure 10:
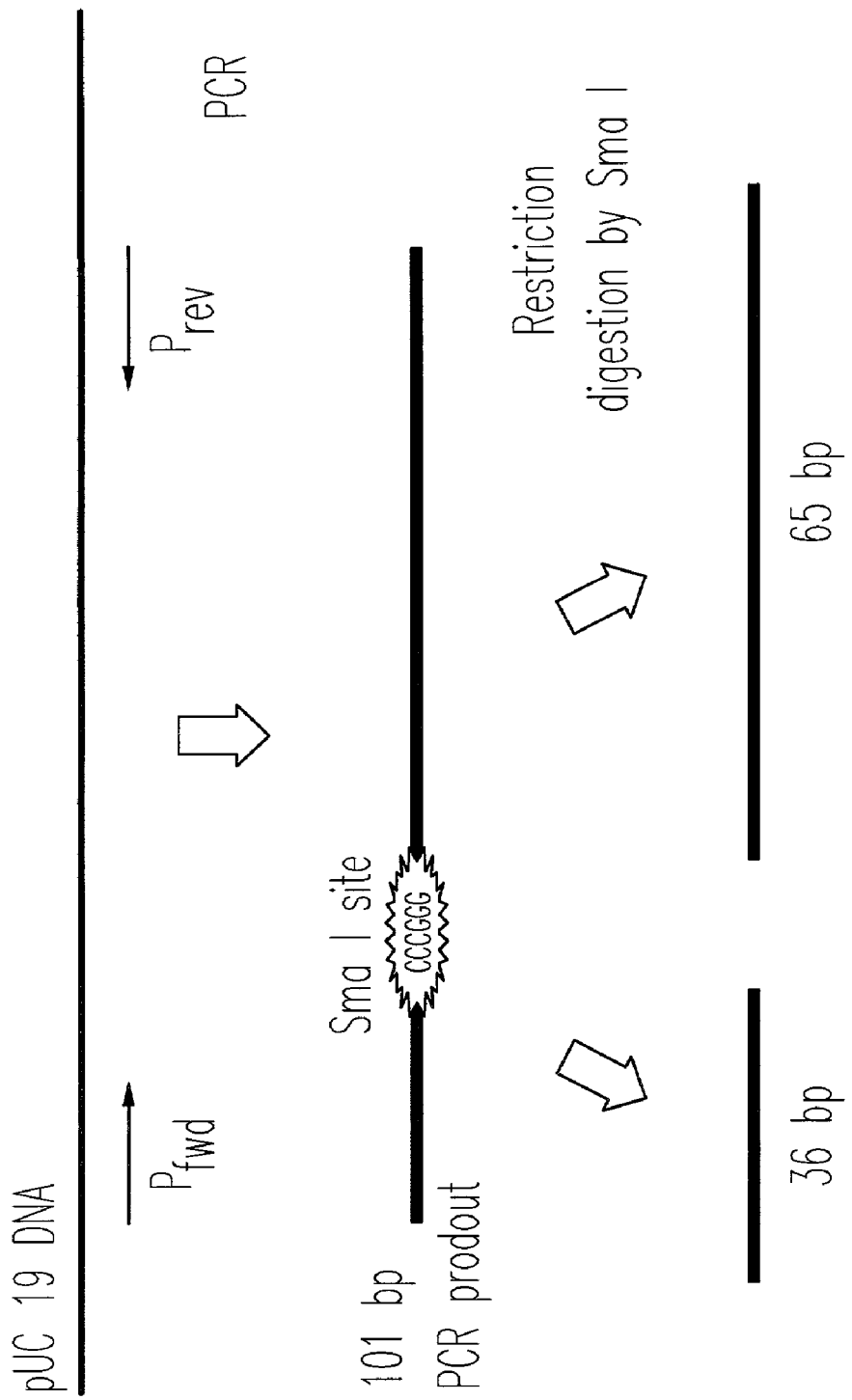
FIG. 10 illustrates a 101 base pair (bp) polymerase chain reaction (PCR) product of a pUC19 DNA, and subsequent cleavage by SmaI into 36 bp and 65 bp fragments.

FIG. 10 depicts the PCR product from Example 1, a pUC19 DNA with Sma I enzyme. This PCR product from Example 1 had one Sma I restriction site resulting in a 36 bp and 65 bp fragment. This system was used as a model to study the characteristics of the membrane mediated restriction digestion.

Example 2

Restriction Digestion

Restriction endonuclease digestion was accomplished on small pore size microfibrous membranes. The digestion process took place within the capillary channel network of the nanoporous membrane. A nanoporous membrane loading comb was utilized. Alternatively, it should be noted that the PCR reaction mixture and product containing membrane used in the PCR amplification can be integrated for use in the restriction digestion. The target polynucleotide was mixed with the restriction enzyme and relevant buffer components and delivered onto the surface of a nanoporous membrane. After incubation for between 1 and 10 minutes at room temperature, the cleaved fragments were analyzed. This example operates with small quantities of reagents (submicroliter) and provides rapid digestion kinetics.

In one embodiment, existing restriction digestion protocols are applied and miniaturized to provide nanoporous membrane mediated restriction digestion. In addition, membrane mediated digestion can be performed on small membrane pieces (mm and sub-mm diameter) that can be interfaced with regular and microfabricated separation devices. Thus, large scale application and multiplexing is supported. The sample and enzyme consumption is reduced using submicroliter volumes of reagents. In addition, this example produced a reduced amount of chemical/biochemical and container (plastic tubes) waste. Due to the reduced reaction volume and reduced distances in the capillary network of the nanoporous membrane, the reaction was accomplished over the course of minutes.

Reaction mixtures containing nanoporous membranes can be stored for future analysis and transported to different locations for downstream processing. Lab space required for the digestion is reduced, also allowing the implementation of handheld devices (on-site digestion). The subject matter allows application of the reaction mixture containing membrane to various regular and microfabricated separation devices.

Initially, 8.8 ng DNA with 2× NE Buffer 4 in a 0.2 µl volume was measured on the tabs of the membrane. This was followed by adding 0.4 µl (20 U/µl=8 U) Sma I restriction endonuclease and then the membrane was put on a 1% agarose block in a tray, and the tray was covered with a glass plate to prevent evaporation and drying of the membrane. After a 0.5 to 10 minute digestion period, the membrane (without sample loading or preparation procedures) was inserted into the ultrathin layer platform and the 36 and 65 bp fragments were separated in approximately 5 minutes. The effective separation length was 4 cm, 750 V.

In one example, the enzyme concentration dependence was measured. The Sma I restriction enzyme was diluted with Diluent A to 1–10 U/µl final concentration. Diluent A contains 50 mM KCl, 10 mM Tris-HCl pH 7.4, 0.1 mM EDTA×$Na_2$, 1 mM DTT, 200 µg/ml BSA and 50% glycerol.

Example 3

Restriction Digestion of ΦX 174 DNA

Figure 11:
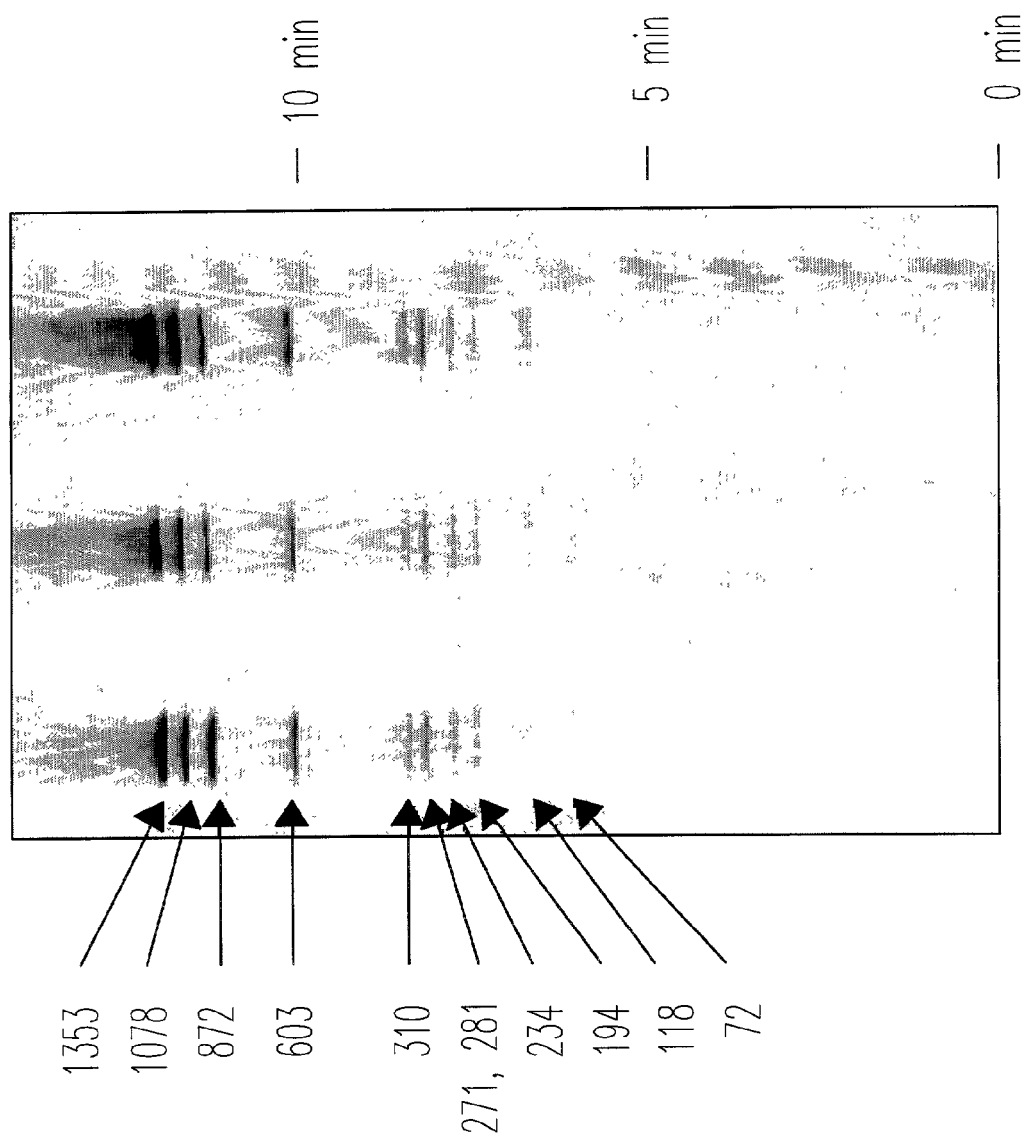
FIG. 11 illustrates electrophoresis analysis of membrane mediated restriction digestion products on an ultra thin layer gel.

FIG. 11 depicts electrophoresis analysis of a membrane mediated restriction digestion products of the ΦX 174 plasmid DNA, which was also accomplished using Hae III restriction endonuclease. 3.2 ng of ΦX 174 DNA with 2× REACT 2 buffer in a total volume of 0.2 µl was measured onto the tabs of the membrane and 0.4 µl (10 U/µl=4 U) Hae III enzyme was added. 10 minute restriction digestion was carried out in the same conditions and separation of the completely digested 11 fragments was accomplished in 12 minutes.

Example 4

Restriction Digestion of Binary Vector Encoding GFP

Figure 12:
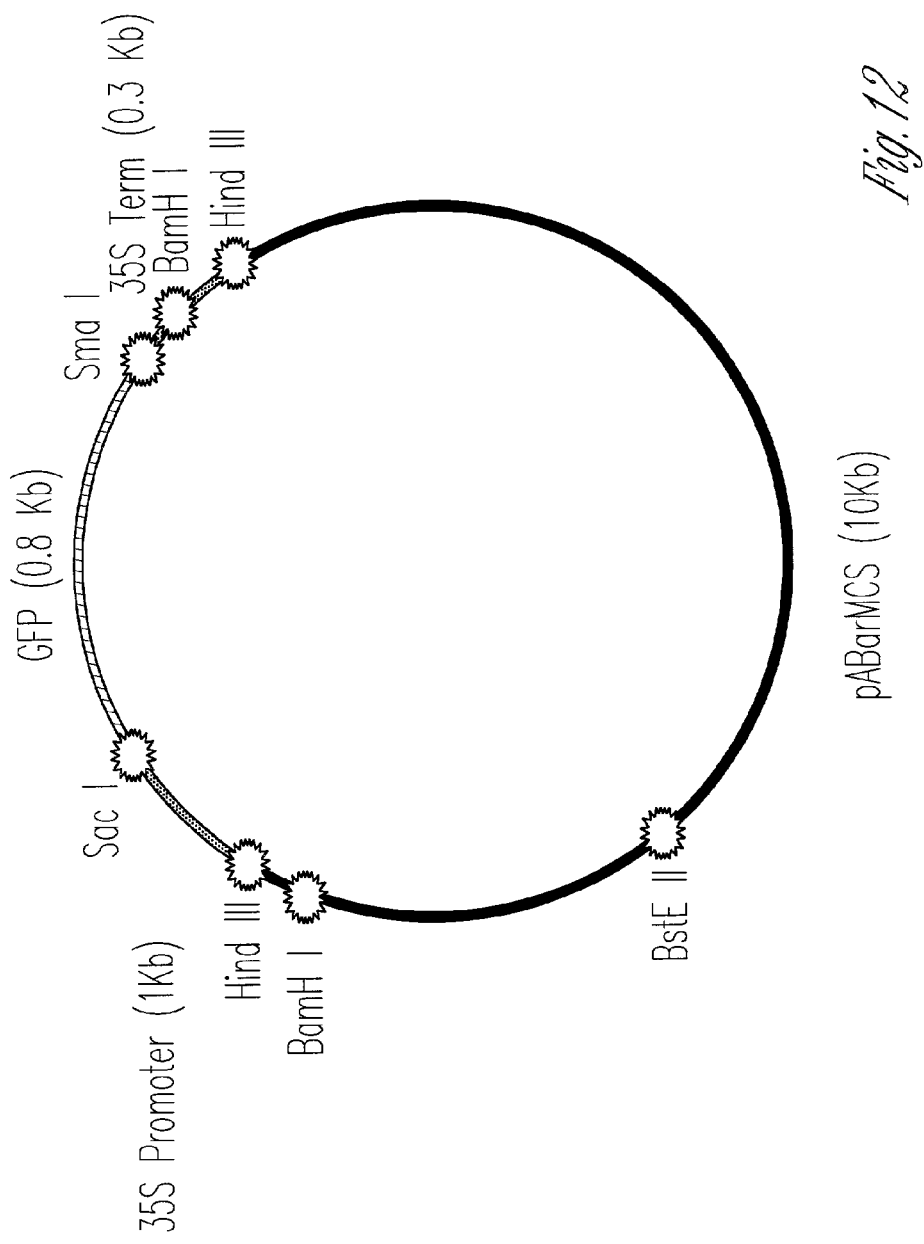
FIG. 12 illustrates a map of a green fluorescent protein (GFP) reporter construct.

FIG. 12 illustrates GFP in a binary vector, which was also used to test the system. The construct was generated by cloning the GFP gene into pRTL2 with Sac I and Sma I digest, to acquire the CaMV 35S promoter and terminator. The expression cassette was released by Hind III digest and ligated into pABarMCS. This construct was digested on the membrane using the BsteE II enzyme (resulting in a 12.4 Kbp product), with Hind III (resulting in a 10.3 and a 2.1 Kbp fragments) and with BamH I (resulting in a 10.6 and a 1.8 Kbp fragments). Simultaneous digestion using Sac I and Sma I enzymes in one step was accomplished resulting in 3 digestion products (11.3 KbP, 0.8 Kbp, 0.3 Kbp).

Figure 13:
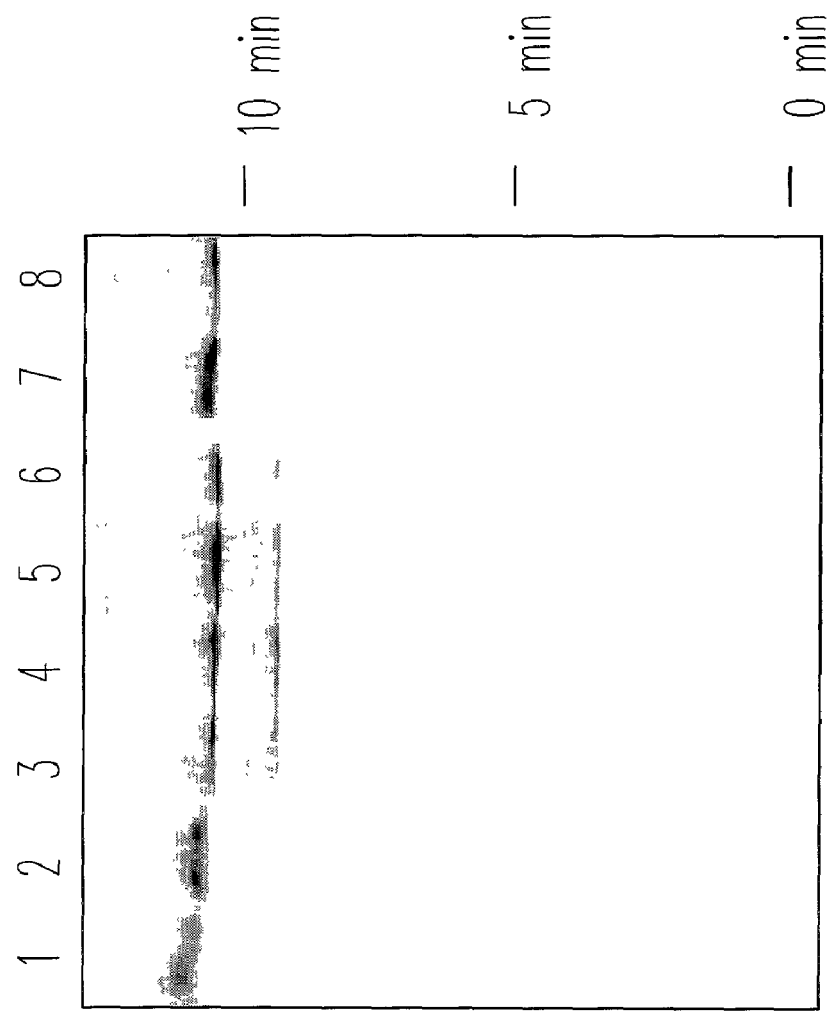
FIG. 13 illustrates an ultra thin layer electrophoresis gel analysis of membrane mediated restriction digest fragments.

FIG. 13 depicts the ultra thin layer gel electrophoresis analysis of the membrane mediated digestion samples. Lanes 1 and 2 show the product of the BstE II digest (11.5 Kbp). Lanes 3 and 4 shows the products of the Hind III digest (10+1.5 Kbp). Lanes 5 and 6 show the products of the BamH I digest (10+1.5 Kbp). Lanes 7 and 8 show the simultaneous digestion products using the Sac I and Sma I enzymes (10.7+0.8 Kbp)

Introduction to Examples 5–11

In Examples 5–9, a nanoporous membrane that is compatible with the specific application is selected. Some factors to be considered when selecting a membrane are the materials from which the membrane is made, the membrane pore size, the shape of the membrane and the design of the membrane. Other factors may also be considered in selecting a nanoporous membrane or structure.

The membrane may be fabricated of various materials. In procedures in which the membrane is treated with nonaqueous organic solvents, strong acids, strong bases or other reactive compounds, the membrane may be fabricated of material that is resistant to such degradation. However, in some applications degradation of the membrane subsequent to the reaction may be desirable. In these cases, a membrane sensitive to the selected degradation agent may be chosen.

The selection of membrane pore size may be important in some applications. For example, if the reaction products can be separated from the reactants by a filtration process that isolates the desired products in the filtrate, a membrane having a pore size that allows passage of the desired products while retaining other reaction components may be selected. Conversely, if the size of the desired products is such that they can be isolated by filtering the excess reactants though the membrane, then a pore size that selectively prevents the passage of the desired product may be selected.

The shape of the membrane may also be an issue for consideration. For example, some applications, such as enzyme assays, may be greatly facilitated by using a number of small membrane disks. Other reactions, such as the radiolabeling of a chemical compound may be performed on a single large membrane sheet. Still other applications may be performed using hollow fiber style membranes. Other shapes or configurations are also contemplated, including, for example, a nanoporous array or nanoporous beads.

The overall design of the membrane may be tailored for a particular application. For example, membrane disks mounted in centrifuge tubes greatly facilitate filtration by centrifugal force. Likewise, customized membrane arrays that are similar in design to a micro-titer plate may be desirable for high throughput applications.

Example 5

Modification of Biomolecules

In one embodiment, the present subject matter is applied to the modification of biomolecules. Such reactions include, but are not limited to, the modification of polypeptides by the addition or the removal of glycosyl, prenyl, acyl, alkyl or phosphoryl groups, the modification of polysaccharides by the addition or the removal of lipids or peptides, and the modification of lipids or polynucleotides by the addition or the removal of small molecules.

To utilize the differential filtration capabilities of the present system, a membrane having a suitable pore size is selected. For some modification reactions, a membrane having a pore size large enough to allow passage of unreacted substrate yet small enough to retain the desired reaction products is selected. Additionally, the shape and design of the membrane is selected to facilitate subsequent manipulations, such as vacuum filtration.

An example of a biomolecular modification reaction using a nanoporous membrane is the phosphorylation of groups of proteins, or peptides, that are sensitive to phosphorylation by a protein kinase, such as mitogen-activated protein (MAP) kinase. In general, the ingredients for a phosphorylation reaction using the disclosed system are 0.01 to 1.0 µg an active preparation of the protein kinase, a substrate for phosphorylation, a reaction buffer containing 20 µM [γ-$^{32}$P] ATP, and a microporous membrane. To perform the reaction, the components are combined and then transferred to the surface of the microporous membrane. Alternatively, the reaction is performed by individually transferring each component to the membrane. The reaction is typically complete within seconds.

In addition to enhancing reaction kinetics, the present system provides a method for separating and analyzing the reaction products. Separation of the phosphorylated polypeptides from the unreacted ATP is achieved by filtering an excess volume of phosphate buffered saline (PBS) or other solution through the membrane. This filtration can be achieved through the use of a standard vacuum filtration device, a high pressure ultrafiltration device, a centrifugal filtration apparatus or other similar filtration device.

After the removal of the unreacted substrate, the reaction products are washed from the membrane and analyzed by radio-HPLC or the membrane section containing the reaction products is directly loaded onto an analytical gel.

Example 6

Determination of Enzymatic Activity

The present system may be used in enzymology applications. The reaction kinetics are enhanced using the present system and, thus, the present system can be used for reducing the time for the assay of enzymes having low activity. The system facilitates reactions in which quantities of enzyme or substrate are limited since it allows reactions to be performed at the sub-microliter scale. As a result of this reduced reaction time and volume, the overall throughput of assays is increased by using this system.

A membrane made of an appropriate material and having an appropriate pore size is selected before performing the reaction. Also, the shape or design of the membrane is selected to facilitate subsequent manipulations.

Once a membrane is selected, the reaction components are added. In one embodiment, the reaction components are combined and then transferred to the membrane. In one embodiment, each component is transferred to the membrane individually. Following the transfer, the reaction is incubated for a period of time before being quenched. The products are then eluted from the membrane and analyzed using conventional methods.

An example of an enzymatic reaction that is performed using nanoporous membranes is the assay of taxadiene synthase. Because the extraction of the olefin reaction product involves a nonpolar organic solvent, a membrane that is resistant to degradation in such solvents is selected. Furthermore, if a sensitive analytical method, such as capillary gas chromatography, is used for product analysis, then the membranes are pre-washed with the product extraction solvent to remove trace contaminants that may interfere with the analysis.

The reaction is initiated by adding 0.01 to 0.2 mg of purified taxadiene synthase to a volume of reaction buffer containing 10 mM [1-$^3$H]geranylgeranyl diphosphate (GGPP) and then transferring the mixture to a small membrane disk. After the reaction is incubated for an appropriate duration, the disk is placed in a small tube with 200 μl of pentane and agitated to remove the radiolabeled taxadiene reaction product. The radiolabeled GGPP substrate as well as the other reaction components remain in the aqueous phase on the membrane disk since they are not soluble in pentane. In one embodiment, radiolabeled taxadiene is recovered by filtration of the pentane through the membrane disk. Filtration through the membrane is achieved through the use of a standard a vacuum filtration device, a high pressure ultrafiltration device, a centrifugal filtration apparatus or other filtration device.

The amount of GGPP converted to taxadiene is measured by using a scintillation counter to determine the amount of radiolabel contained in the pentane fraction. In one embodiment, the radiolabeled taxadiene is concentrated by reducing of the volume of pentane under a stream of argon and then analyzed by capillary gas chromatography.

Another example of an enzymatic reaction that is applied to nanoporous membranes is the assay of 5-lipoxygenase (5-LO). As with the taxadiene synthase reaction, the membrane used in this reaction is exposed to organic solvents, and thus, a membrane that is resistant to degradation by such solvents is selected. Where reversed-phase HPLC is used to analyze the reaction products, the membranes typically are pre-washed with the product extraction solvent to remove trace contaminants that may interfere with the analysis.

The reaction is initiated by adding 0.01 to 2 mg of a nuclear membrane preparation containing 5-LO to a volume of reaction buffer containing 20 mM arachidonic acid and then transferring the mixture to a small membrane disk that is housed in a syringe adaptable filtration unit. After an incubation period, the reaction is stopped by the addition of a volume of 1N citric acid that corresponds to 5% of the original reaction volume. The leukotriene reaction products and the arachidonic acid substrate are subsequently extracted by using a syringe to force two 100 μl aliquots of hexane/ethyl acetate (1:1) through the membrane. In one embodiment, internal standards are added to the pooled organic extract before drying under a stream of argon. The residue is redissolved in a small volume of HPLC grade methanol/water (1:1) containing 5% acetic acid then analyzed by reversed-phase HPLC.

Example 7

Determination and Quantitation of Protein-molecule Binding Reactions

The present system is used to study protein-molecule binding reactions. Typical examples of protein-molecule binding reactions include, but are not limited to, receptor-ligand binding, antibody-antigen binding, protein-nucleotide binding, enzyme active sites inhibitor binding and protein prosthetic group binding.

The use of nanoporous membranes in protein-molecule binding reactions increases the overall speed of these analyses. The reaction incubation time is decreased as a result of the increased reaction kinetics provided by the membrane system. Furthermore, in some protein-molecule binding applications, the reaction products are rapidly isolated by utilizing the differential filtration properties of these membranes.

The membrane pore size and membrane design are considerations when selecting the microporous membrane for protein-molecule binding reactions. To utilize the differential filtration capabilities of these membranes, a membrane having an appropriate pore size is selected. For some protein-molecule binding reactions, the bound protein-molecule complex are retained on the filter while unbound molecule is washed through. Accordingly, in such reactions, a pore size that prevents passage of protein-molecule complex through the membrane while allowing the passage of unbound molecule is selected. In addition to the selection of pore size, the shape and design of the membrane is selected to facilitate subsequent manipulations, such as vacuum filtration.

An example of a protein-molecule binding reaction performed using the present system is the receptor-ligand binding reaction. Receptor-ligand binding reactions are used for a number of purposes, including but not limited to, detecting the presence of a ligand in a sample, determining receptor specificity, determining the affinity of the receptor for various ligands, and determining the number of receptor binding sites.

To assist in the detection and quantitation of the receptor-ligand complex, the ligand is labeled. Typical radiolabeling protocols are known in the art. (See, for example, the following publication, which is incorporated herein by reference: "Biomembrane Protocols II. Architecture and Function", J. M. Graham and J. A. Higgins, eds., 1994, Humana Press, Totowa, N.J. (Chapter 24)).

The receptor-ligand binding reaction is initiated by adding 0.005 to 0.1 mg of purified receptor to a volume of binding buffer containing between 0.05 and 5 nM $^{125}$I-labeled ligand then transferring the mixture to a membrane disk that is mounted in a vacuum filtration device. In one embodiment, each component is added to the disk individually. After incubation for an appropriate duration, unbound $^{125}$I-labeled ligand is vacuum filtered through the membrane with an excess of PBS or other wash solution. The membrane, which contains the radiolabeled receptor-ligand complexes, is then removed from the filtration unit and the radioactivity is quantified with a gamma counter.

The method for separation of unbound $^{125}$I-labeled ligand from the receptor-ligand complexes is not limited to vacuum filtration. High pressure filtration, centrifugal filtration and other methods may be used.

Example 8

Labeling of Biomolecules and Organic Compounds

The present system is applicable to reactions used for labeling of biomolecules and organic compounds. Examples of such labeling reactions include, but are not limited to, labeling of membrane associate biomolecules, labeling of antibodies, labeling of organic tracer compounds, and labeling of synthetic organic reaction products. Both radioactive and nonisotopic labels are used with some labeling reactions.

In various embodiments, nanoporous membranes are used for both large and small scale labeling reactions. In some cases, the nanoporous membrane system enhances the kinetics of these reactions. Furthermore, in some biomolecular labeling applications, labeled products are isolated by utilizing the differential filtration properties of these membranes. In some cases, the isolation of small organic products can involve additional separation techniques.

Before performing the labeling reaction, a membrane material is selected. For example, organic solvents are used for some labeling reactions. A membrane resistant to degradation by such solvents is selected for use in these reactions.

In one embodiment, a membrane pore size is selected. For example, in biomolecular labeling applications, a membrane pore size that selectively prevents passage of the desired product is selected.

An example of a labeling reaction that is performed using nanoporous membranes involves the labeling of transmembrane glycoproteins contained in lipid vesicles. For such reactions, a membrane having a pore size small enough to retain labeled lipid vesicles but large enough to pass unreacted labeling substrate is selected. In one embodiment, involving a large scale preparation, a large membrane disk is mounted in a high pressure filtration device.

A lipid vesicle glycoprotein labeling reaction is initiated by adding 0.01 to 100 mg of a lipid vesicle preparation containing glycoprotein to a volume of 1.2 mM NaIO$_4$ and then transferring the mixture to a membrane disk. The membrane is then incubated for an appropriate duration. After incubation, the membrane is placed in an ultrafiltration device and a large excess of PBS or other wash solution is passed through the membrane by using pressurized filtration. When the membrane reaches near dryness, a volume of 1.2 mM [$^3$H]NaBH$_4$ is added. After incubation for an appropriate duration, an excess volume of wash solution is once again passed through the membrane by using pressurized filtration. The labeled lipid vesicle glycoproteins are recovered by washing the surface of the membrane after removing it from the filtration device.

The method for separation of unreacted [$^3$H]NaBH$_4$ from the labeled vesicle preparation is not limited to high pressure filtration. Vacuum filtration, centrifugal filtration and other methods may be used.

Example 9

Selective Modifications of Chemical Compounds

The present system is applicable to reactions involving selective modifications of chemical compounds. Examples of such reactions include, but are not limited to, regio-specific covalent modification and cleavage reactions, stereo-specific covalent modification and cleavage reactions, and directed molecular rearrangement reactions.

The capability for high throughput is helpful in some selective modification reactions. For example, high throughput is helpful when different reaction conditions are tested in order to achieve a desired reaction specificity. In one embodiment, a nanoporous membrane in selective modification reactions increases overall throughput by increasing the speed of product formation and allowing reactions to be performed at the sub-microliter scale.

Before performing the selective modification reaction, a suitable membrane material is selected. For example, some selective modification reactions are performed in organic solvents. A membrane resistant to degradation by such solvents is selected for use in these reactions.

Consideration of the shape and design of the membrane may also be helpful. In certain applications, several variations of certain selective modification reactions may be performed in order to achieve desired reaction specificity. If the reaction scale is small, assays may be conveniently performed on a series of small membrane disks.

An example of a selective modification reaction that can be used with nanoporous membrane is the regio-specific acetylation of Baccatin III. To test the regio-specificity of this acetylation reaction, several small membrane disks are used. A membrane material resistant to degradation by organic solvents is selected. Since gas chromatography-mass spectrometry (GC-MS) is used to analyze the reaction products, the membranes are pre-washed with the product extraction solvent to remove trace contaminants that may interfere with the analysis.

Parameters that typically affect reaction specificity, such as temperature, length of incubation, and substrate concentration are varied. The reactions are initiated by adding 0.01 to 1.0 mg of Baccatin III and reactive amounts of acetic anhydride to a volume of Cl$_2$CH$_2$ containing catalytic amounts of dimethylaminopyridine (DMAP) and then transferring the mixture to membrane disks. Each membrane containing a reaction is then incubated at a different temperature for an appropriate duration.

Reaction products are obtained by placing the membrane disk into a separate tube and extracting the reaction components into hexane/ethyl acetate (1:1). The relatively non-polar reaction products are then separated from the relatively polar reactants by passing the extract over a short column of silica gel. The eluted products are concentrated by reducing the volume of hexane/ethyl acetate under a stream of argon and then analyzed by GC-MS.

Example 10

Chemical Reactions Involving Metals

The present system is applicable to chemical reactions involving metals (CRIMs). Examples of such reactions include, but are not limited to, the reaction of cyclic organic compounds with metal acids, the detection of trace metals and metal-ligand substitution reactions.

In one embodiment, a nanoporous membrane used with CRIMs decreases the incubation time for product formation because of the enhanced reaction kinetics that the membrane system provides.

Before performing a CRIM, a suitable membrane material is selected. For example, the solvents required for some CRIMs are strongly acidic, thus, a membrane resistant to degradation by strong acids is selected.

An example of a typical CRIM that can be performed using the present system is the detection of codeine with niobic acid. For such a reaction, a membrane resistant to strong acids is selected. If the reaction is to be performed with numerous samples, then arrays containing multiple membrane disks may be used.

In one embodiment, the reaction is performed in two steps. First, the sample suspected of containing codeine is dissolved in an amount of glacial acetic acid and then transferred to the membrane. Next, a 1% solution of niobic (V) acid in 85% orthophosphoric acid is applied. In one embodiment, the codeine sample and niobic acid are combined and then applied to the membrane. In one embodiment, the membrane is incubated for an appropriate duration. Formation of a black spot on the membrane indicates the presence of codeine.

Consider next the detection of traces of iron using 2-nitroso-1-naphthol. For such a reaction, a membrane that is resistant to organic solvents is selected. If the reaction is to be performed with numerous samples, arrays containing multiple membrane disks may be used.

In one embodiment, the reaction is performed in two steps. First, the sample that is suspected to be contaminated with iron is applied to the membrane. In one embodiment, if the sample is a solid object, the membrane is swiped over the surface of the object. In one embodiment, if the sample is a solution, an appropriate volume is applied to the membrane surface. Next, a 0.5% solution of 2-nitroso-1-naphthol prepared in acetone is sprayed onto the membrane surface. In one embodiment, the membrane is incubated for an appropriate duration. Formation of a dark green color on the surface of the membrane indicates the presence of iron.

Example 11

Combinatorial Chemistry

The present system may be used in combinatorial chemistry applications. Examples of combinatorial chemistry applications include, but are not limited to, synthesis of combinatorial libraries, optimization of combinatorial reactions and automated high throughput synthesis of combinatorial libraries.

High throughput capability may be helpful in some combinatorial chemistry applications. As the size of the libraries and complexity of the syntheses increases, the benefits of increased throughput becomes greater. High throughput capability may also be helpful when there are numerous different reaction conditions to be tested in order to achieve optimum reaction conditions. One embodiment of the present system enhances throughput by increasing the speed of product formation and by allowing reactions to be performed on a sub-microliter scale.

Before performing a combinatorial chemistry application, a suitable membrane material is selected. For example, some combinatorial chemistry applications are performed in organic solvents and thus, a membrane resistant to degradation by such solvents is selected.

Consideration of the size and shape of the membrane may be helpful. In one embodiment, the reactions are performed on a single membrane sheet. In other applications, reactions are performed on several small membrane disks or on the surface of hollow tube membranes.

An example of a combinatorial chemistry application that is performed using the present system is the synthesis of a 2-aminothiazole library. A membrane resistant to degradation by organic solvents is selected. Also, to prevent contamination of the library with membrane components, the membrane is pre-washed with the solvents that are used in the library synthesis.

The synthesis of the 2-aminothiazole library is initiated by adding reactive quantities of a mixture of primary thioureas to reactive quantities of a mixture of α-bromoketones in a volume of DMF and then transferring the mixture to a membrane disk. The membrane disk is then incubated at an elevated temperature for an appropriate duration.

Reaction products are obtained by placing the membrane disk into an extraction vessel and then extracting the reaction components into a solvent system, such as chloroform/methanol (1:2). The quality of the synthesis is determined by a combination of spectroscopic techniques.

Other Embodiments

The present subject matter relates to a nanoporous structure or membrane, however, a microporous structure or membrane may also be used. The pores of a microporous structure or membrane are larger than those of a nanoporous structure.

Figure 14:
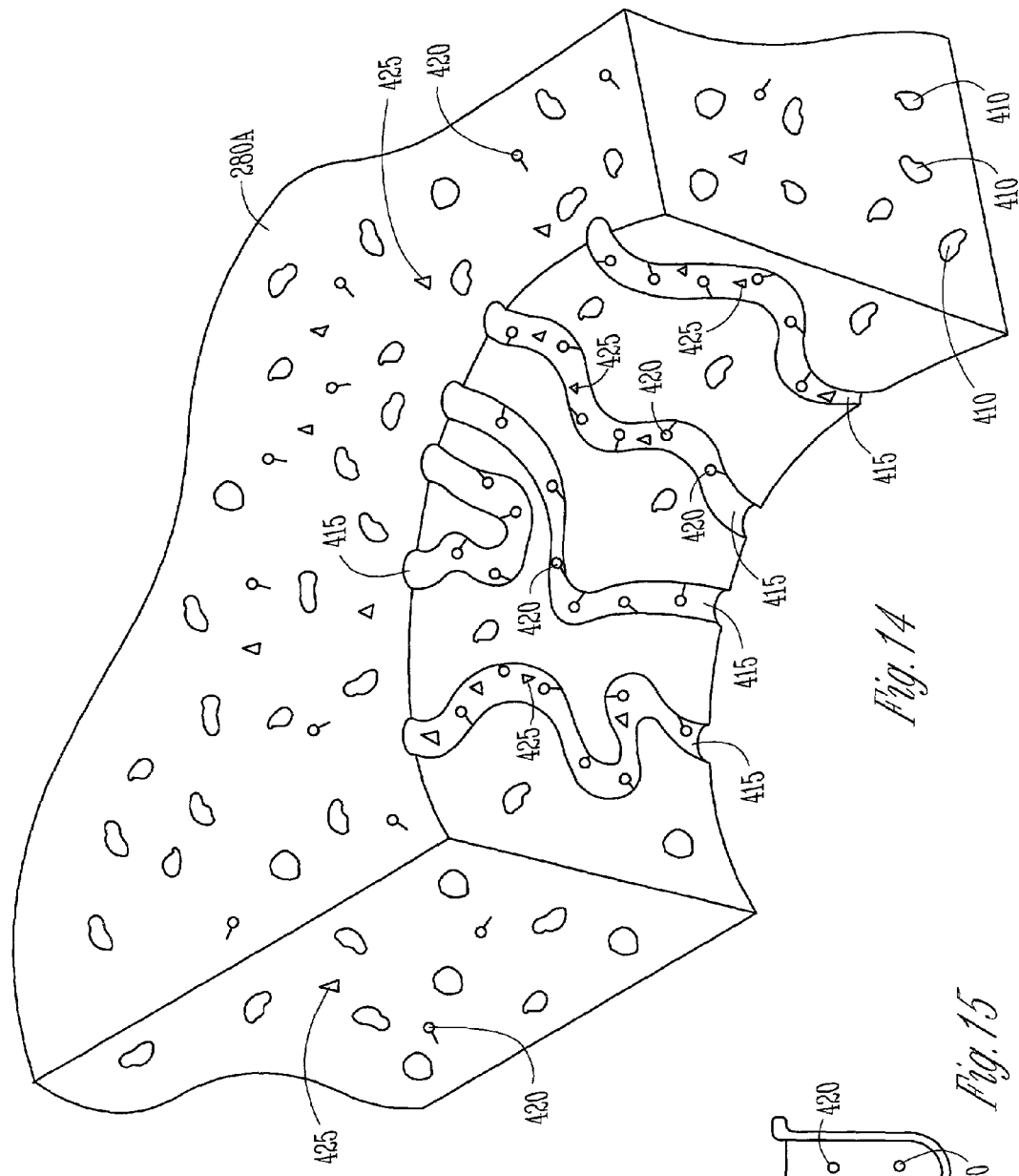
FIG. 14 illustrates a cut-away view of a model of a portion of a nanoporous structure.

FIG. 14 illustrates a cut-away view of a portion of nanoporous structure 280A according to one embodiment. The figure depicts a number of pores 415 exposed in the cut-away portion and a number of pore openings, or orifices, 410 on the different surfaces of structure 280A. Pores 415 are generally circular in cross-section, however they may be oval or other shapes as well. In one embodiment, pores 415 are distributed throughout structure 280A in a labyrinthian style. In one embodiment, pores 415 are arranged in an orderly manner. The figure illustrates each pore having two orifices however, a pore may have zero, one, two or more orifices or openings terminating on a surface of structure 280A. In one embodiment, the porous structure includes non-woven material having entangled fibers or filaments. The orifices and pores of a non-woven structure are randomly shaped.

Distributed throughout the interior walls and external surfaces of structure 280A are a number of elements 420 and elements 425. Element 420 may represent an enzyme, a substrate, a catalyst or other component as part of a reaction. In the figure, elements 420 are shown bonded to a surface of structure 280A. Elements 425 are shown to be distributed throughout structure 280A, some of which may bond with elements 420 within the reduced confines of the pores 415. In one embodiment of the present subject matter, elements 420 and 425 migrate into portes 415 under the influence of capillary action. In one embodiment, the reaction proceeds to completion by virtue of molecular crowding arising from an increased effective concentration within nanoporous structure 280A.

Figure 15:
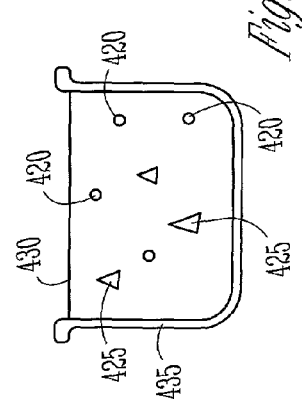
FIG. 15 illustrates a cut-away view of a beaker with modeled components in a mixture.

FIG. 15 illustrates a model of a beaker with modeled elemental components in a mixture. In the figure, the mixture level is denoted by 430 and includes element, or component, 420 and element, or component, 425. In the relatively large vessel of beaker 435, component 420 and component 425 are at low effective concentration and the reaction producing a product progresses at a rather low rate. In one embodiment of the present system, a nanoporous structure is inserted into beaker 435 and establishes contact with mixture 430. Elements 420 and 425 migrate into the pores of the nanoporous structure and the reaction proceeds under enhanced kinetic factors. For example, in one embodiment, the rate of diffusion is increased by the addition of the nanoporous structure and the product resulting from the components is produced at a faster rate.

Figure 16:
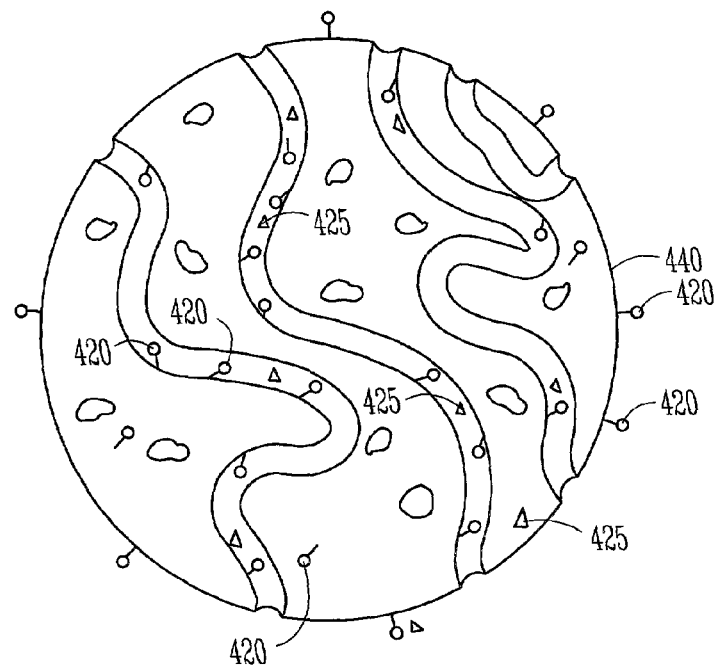
FIG. 16 illustrates a cut-away view of a model of a portion of a nanoporous structure in the form of a bead.

FIG. 16 illustrates a cut-away view of a model of a portion of a nanoporous structure in the form of a bead. In the figure, nanoporous structure 440 includes a spherical bead having a network of pores 415 distributed throughout the interior and a number of pore openings, or orifices, 410 appearing on the surface of structure 440. Structure 440 is shown as a bead however, other shapes are also contemplated, including ellipsoid or other geometrical shapes.

One embodiment includes a plurality of nanoporous beads in a column or other vessel. In such an embodiment, the component, or components to be reacted are introduced to the column or vessel. The nanoporous beads of the present subject matter reduces the diffusion limitation resulting in one or more enhanced kinetic factors.

The figure also illustrates a plurality of elements 420 affixed to portions of structure 440, however, in one embodiment, elements 420 are unattached and migrate freely throughout structure 440. Elements 425 are illustrated throughout structure 440.

Figure 17:
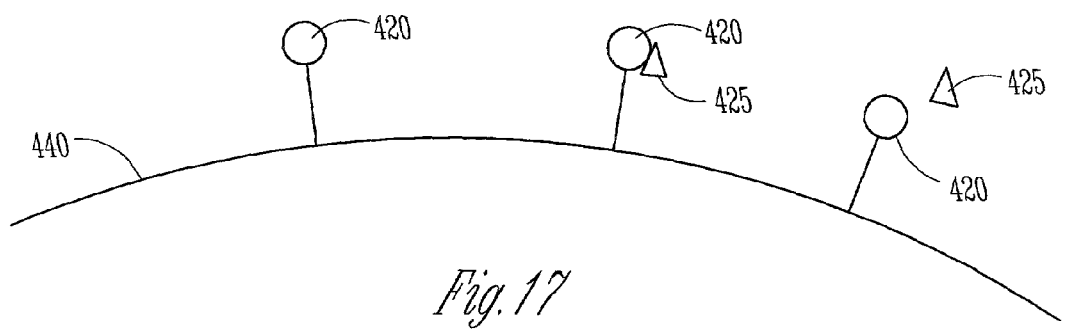
FIG. 17 illustrates a view of a portion of the model in FIG. 16.

FIG. 17 illustrates a view of a portion of the model in FIG. 16. In the figure, elements 420 are affixed to an exterior or interior (walls of the pores) surface of nanoporous structure 440. Elements 425 are in a solution and, when placed in the environment of the nanoporous structure, bond to elements 420. According to one theory, the bonding is accelerated by the increased effective concentration of components within the confines of the nanoporous structure 440.

Figure 18:
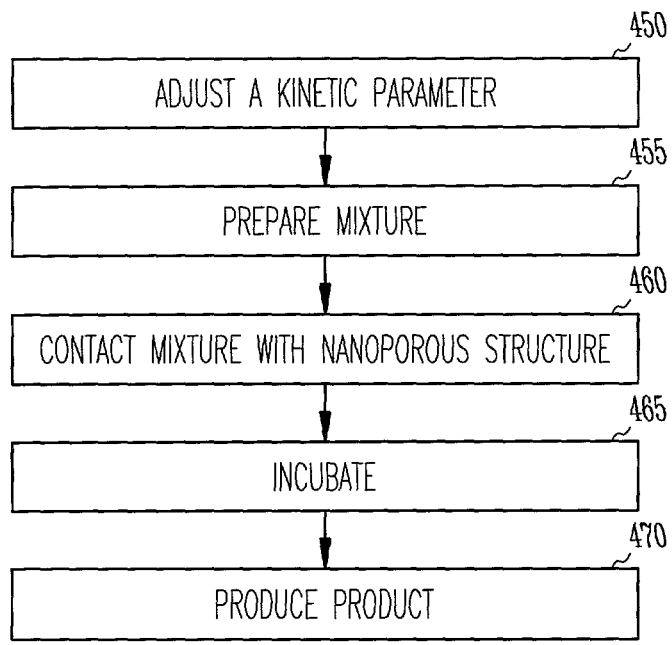
FIG. 18 illustrates a flow chart of a method operable with the present system.
Figure 19:
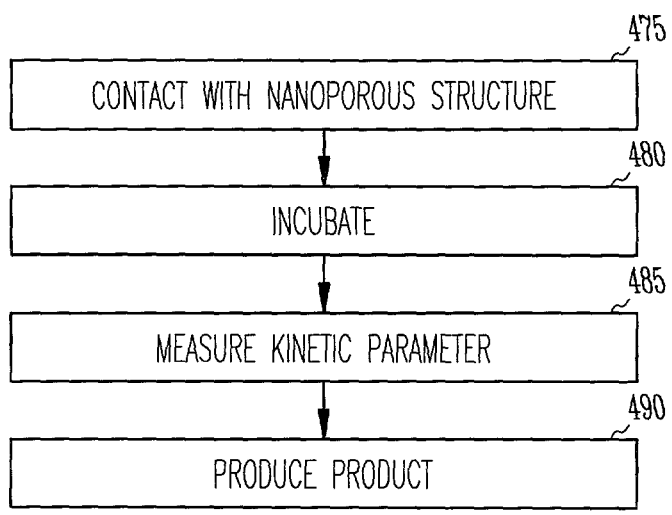
FIG. 19 illustrates a flow chart of a method operable with the present system.

Methods according to the present subject matter are presented in FIGS. 18 and 19. By way of contrast, the method of FIG. 18 entails adjusting an external kinetic factor in the course of producing the product of the reaction and the method of FIG. 19 entails producing the product of the reaction under conditions that produces a change in a kinetic factor. In each method, the particular steps may be performed in an order that differs from that shown.

FIG. 18 illustrates a flow chart of a method operable with one embodiment of the present system. At 450, the method allows the operator to adjust a kinetic parameter. For example, the reaction using the present system may proceed at a temperature lower than that when performed without the present system, and thus, at 450, the temperature is lowered. At 455, a mixture is prepared using a first and second component. In one embodiment, the mixture includes a single component in a solution. At 460, the mixture is brought into contact with a nanoporous structure. In one embodiment, the nanoporous structure includes a reaction component or catalyst coating the nanopores of the structure. In one embodiment, the material of the nanoporous structure does not chemically interact with the mixture. At 465, the nanoporous structure, along with the mixture, is incubated for a period of time. In various embodiments, the incubation period ranges from zero seconds to hours or days. In one embodiment, the incubation period includes application of heat, refrigeration, pressure, vacuum or other external factor. At 470, the product of the reaction is produced.

FIG. 19 illustrates a flow chart of a method operable with the present system. At 475, the mixture is brought into contact with the nanoporous structure. In one embodiment, the mixture includes a single reaction component. In one embodiment, the mixture includes two or more reaction components. In one embodiment, bringing into contact entails applying the mixture to the nanoporous structure in a manner that allows the mixture to migrate into the nanoporous structure by capillary action or other forces. At 480, the system of the nanoporous structure with the mixture is incubated for a period of time and under conditions conducive to production of the product. At 485, a changed kinetic factor is detected and measured and at 490, the reaction product is produced. For example, in one embodiment, the production of a reaction product occurs more rapidly using the nanoporous structure than if not using the nanoporous structure, and in this case, the changed kinetic factor is an increased rate of reaction. Thus, the measured kinetic parameter is a reduced reaction time.

CONCLUSION

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A method comprising:
contacting a first component and a second component with one of a nanoporous membrane comprising pores and a nanoporous bead comprising pores, wherein the first and second components are contacted within the pores; and producing a product from a reaction of the first component with the second component.

2. The method of claim 1 further including incubating the first component with the second component.

3. The method of claim 1 further comprising mixing the first component with the second component.

4. The method of claim 1 further comprising immobilizing the first component to the nanoporous structure.

5. The method of claim 1, wherein contacting the first component and the second component with the nanoporous structure includes increasing an effective concentration.

6. The method of claim 1 further comprising adjusting a kinetic parameter.

7. The method of claim 6, wherein adjusting a kinetic parameter includes adjusting a temperature, adjusting a concentration, adjusting a time period, adjusting a pH, adjusting a volume, adjusting a pressure, adjusting a diffusion rate, adjusting a material property, adjusting an atmospheric humidity or adjusting a light exposure.

8. The method of claim 1, wherein contacting the first component with the nanoporous structure includes contacting a catalyst with the nanoporous structure.

9. The method of claim 8 wherein contacting the catalyst includes contacting an enzyme, contacting a platinum powder, or contacting a metal complex.

10. The method of claim 9 wherein contacting the enzyme includes contacting a restriction enzyme, contacting a ligase, contacting a polymerase, contacting a kinase, contacting an amylase, contacting an esterase, contacting a dehydrogenase, contacting a transferase, contacting a synthetase, contacting a synthase, contacting a polymerase, contacting a carboxylase, contacting a reductase, contacting a phosphorylase, contacting a phosphotransferase, contacting an aminotransferase, contacting an oxidase, contacting an isomerase, contacting a deamidase, contacting a fumarase, contacting an anhydrase, contacting a dismutase, contacting a peptidase, contacting an aldolase, contacting an enolase, contacting a luciferase, contacting a urease, contacting a galactosidase, contacting a transcarbamylase, contacting a glucosidase, contacting a glucanase, contacting an endonuclease or contacting an exonuclease.

11. The method of claim 1 further comprising contacting a third component with the nanoporous structure.

12. The method of claim 1, wherein contacting a first component includes contacting an antibody, contacting an antigen, contacting a receptor, contacting a substrate, contacting a protein, contacting an amino acid, contacting a nucleic acid, contacting a nucleotide, contacting a lipid, contacting a fatty acid, contacting a carbohydrate, contacting a hydrocarbon, contacting a cofactor, contacting a redox reagent, contacting an acid, contacting a base, contacting a cellular fraction, contacting a subcellular fraction, contacting a virus sample, contacting a fragment of a virus, contacting a buffer, contacting water or contacting an organic solvent.

13. The method of claim 1, wherein producing the product includes producing a modified nucleic acid, a nucleotide, an amplified nucleic acid fragment/sequence, a modified polypeptide, an amino acid, a cleavage product, an antibody/antigen complex, a ligand/receptor complex, an immunoassay product, a modified chemical, a sequencing fragment, a primary metabolite or a secondary metabolite.

14. The method of claim 13 wherein producing the cleavage product includes producing a nucleic acid fragment, a nucleotide, a polypeptide, an amino acid, a fatty acid, a carbohydrate, a polysaccharide, a simple sugar, a primary metabolite or a secondary metabolite.

15. The method of claim 2, wherein producing the product includes producing an amplified nucleic acid fragment and wherein incubating includes applying a series of temperature changes appropriate for sequence amplification.

16. The method of claim 1, wherein the pores have a diameter ranging from about 1 nm to about 1 $\mu$m.

17. The method of claim 16, wherein the pores have a diameter ranging from about 1 nm to about 100 nm.

18. The method of claim 2, wherein the incubating is for a time period less than that required for a reaction taking place in a non-nanoporous structure.

* * * * *